United States Patent
Ohtsuka et al.

(10) Patent No.: US 7,981,513 B2
(45) Date of Patent: Jul. 19, 2011

(54) DENTAL FILLER

(75) Inventors: Keisuke Ohtsuka, Kitakyushu (JP);
Hirokazu Tanaka, Kitakyushu (JP);
Eiko Tanaka, legal representative, Kitakyushu (JP)

(73) Assignee: JGC Catalysts and Chemicals Ltd., Kawasaki-shi, Kanagawa (JP)

( * ) Notice: Subject to any disclaimer, the term of this patent is extended or adjusted under 35 U.S.C. 154(b) by 154 days.

(21) Appl. No.: 12/312,295

(22) PCT Filed: Sep. 13, 2007

(86) PCT No.: PCT/JP2007/067799
§ 371 (c)(1),
(2), (4) Date: May 5, 2009

(87) PCT Pub. No.: WO2008/056485
PCT Pub. Date: May 15, 2008

(65) Prior Publication Data
US 2010/0056664 A1 Mar. 4, 2010

(30) Foreign Application Priority Data
Nov. 7, 2006 (JP) ................. 2006-302166

(51) Int. Cl.
*B32B 15/02* (2006.01)
(52) U.S. Cl. ...................... 428/403; 428/404
(58) Field of Classification Search .......... 106/482, 106/446, 457, 445, 490, 403, 404, 405
See application file for complete search history.

(56) References Cited

U.S. PATENT DOCUMENTS

| | | | |
|---|---|---|---|
| 4,059,658 A * | 11/1977 | Shoup et al. | 264/43 |
| 4,065,317 A * | 12/1977 | Baak et al. | 501/70 |
| 4,217,264 A * | 8/1980 | Mabie et al. | 523/218 |
| 4,350,532 A * | 9/1982 | Randklev | 106/31.95 |
| 4,358,549 A * | 11/1982 | Randklev | 523/117 |
| 4,431,451 A * | 2/1984 | Mabie et al. | 106/35 |
| 4,503,169 A * | 3/1985 | Randklev | 523/117 |
| 4,880,689 A * | 11/1989 | Park et al. | 428/143 |
| 5,110,637 A * | 5/1992 | Ando et al. | 428/34 |
| 5,139,760 A * | 8/1992 | Ogawa et al. | 423/328.1 |
| 5,209,835 A * | 5/1993 | Makino et al. | 204/192.16 |
| 5,399,435 A * | 3/1995 | Ando et al. | 428/428 |
| 5,464,674 A * | 11/1995 | Makino et al. | 428/834 |
| 5,846,310 A * | 12/1998 | Noguchi et al. | 106/482 |
| 5,852,096 A * | 12/1998 | Heindl et al. | 524/492 |
| 6,730,156 B1 * | 5/2004 | Windisch et al. | 106/35 |
| 6,849,112 B2 * | 2/2005 | Nishida et al. | 106/35 |
| 7,022,447 B2 * | 4/2006 | Miyakawa | 430/108.6 |
| 7,115,349 B2 * | 10/2006 | Iida et al. | 430/108.24 |
| 7,122,078 B2 * | 10/2006 | Frese et al. | 106/31.6 |
| 2004/0096765 A1 * | 5/2004 | Miyakawa | 430/108.6 |
| 2004/0137353 A1 * | 7/2004 | Iida et al. | 430/108.24 |
| 2005/0113480 A1 * | 5/2005 | Usuki et al. | 523/116 |
| 2005/0137283 A1 * | 6/2005 | Frese et al. | 523/160 |
| 2007/0060668 A1 * | 3/2007 | Schoenefeld et al. | 523/160 |
| 2007/0125269 A1 * | 6/2007 | Nishi | 106/481 |
| 2009/0253825 A1 * | 10/2009 | Ohtsuka et al. | 523/116 |
| 2010/0056664 A1 * | 3/2010 | Ohtsuka et al. | 523/116 |
| 2010/0089286 A1 * | 4/2010 | Craig et al. | 106/35 |

FOREIGN PATENT DOCUMENTS

| | | | |
|---|---|---|---|
| EP | 219769 A * | 4/1987 | |
| EP | 221405 A * | 5/1987 | |
| EP | 1041040 A2 * | 10/2000 | |
| EP | 2 002 819 A1 | 12/2008 | |
| JP | 2008115060 A * | 5/2008 | |

* cited by examiner

*Primary Examiner* — James Seidleck
*Assistant Examiner* — Peter A Salamon
(74) *Attorney, Agent, or Firm* — Leydig, Voit & Mayer, Ltd.

(57) ABSTRACT

A dental filler having the optical and/or mechanical properties satisfying the requirements to a dental material, a method for producing the dental filler, and a dental composite material containing the dental filler. The dental filler comprises microparticles of amorphous inorganic oxide constituted by at least silica-based fine particles covered with a composite oxide comprising zirconium, silicon and oxygen. The dental composite material contains the dental filler and a hardenable resin selected from an acrylic resin, a methacrylic resin, an epoxy resin, a vinyl resin and a urethane resin.

9 Claims, 2 Drawing Sheets

DENTAL FILLER

BACKGROUND OF THE INVENTION

1. Technical Field

The present invention relates to a dental filler comprising microparticles of amorphous inorganic oxide prepared by covering surfaces of silica-based fine particles with a composite metal oxide, a method for producing such dental filler, and also a dental composite material containing the dental filler and a hardenable resin.

2. Background Technology

Generally, raw materials for preparing dental fillers are required to have a sufficient strength or hardness equivalent to those of natural teeth, a surface smoothness and a sufficient resistance against abrasion as caused by teething, and therefore silica-based fine particles have been used as a raw material for the dental fillers. Furthermore, the dental fillers are required to have compatibility in color tone with natural teeth, conformity in a refractive index for providing transparency equivalent to that of natural teeth, and an X-ray radiopacity enabling differentiation of a portion treated or repaired with the dental materials from a tooth tissue of natural teeth, and therefore zirconium oxide is also used as a raw material for the dental fillers.

Various examples of the dental fillers are disclosed in publicized documents, for instance, (1) the dental filler which is prepared by aggregating silicon dioxide and other metal oxide (such as zirconium oxide) and then subjecting the aggregated ones to a thermal treatment at a temperature not causing crystallization of the metal oxides, to obtain the aggregated particles of amorphous inorganic oxides such as silicon dioxide and other metal oxide (Refer to Patent document 1), and (2) the dental filler containing a substantially amorphous cluster constituted by fine particles of non-heavy metal oxide (such as silica particles) having the average diameter of less than about 100 nm and fine particles of heavy metal oxide (such as zirconium oxide particles) having the average diameter of less than about 100 nm (Refer to Patent document 2).

However, because the above dental fillers are prepared by mixing a silica sol (as a non-heavy metal oxide) and an aqueous solution of zirconium salt (as a source of a heavy metal oxide), drying the mixture solution with use of a spray drier or the like and then calcining the dried materials, they are obtained as the aggregated particles of amorphous einorganic oxides such as silicon dioxide and zirconium oxide having different refractive indexes. As a result, the refractive indexes measured in samples of the aggregated particles are not equal and inconsistent. Therefore, it is difficult to improve the transparency at the treated or repaired portion of a tooth (including an artificial tooth). Furthermore, the pore volumes of the aggregated particles and also the strength thereof are not adjustable to a desired value. Moreover, because the adhesiveness of the aggregated particles to hardenable resins is insufficient, the strength and the hardness at the treated or repaired portion of a tooth (including an artificial tooth) are lowered, which may lead to insufficient resistance of the dental fillers against abrasion as caused by teething.

To solve the problems as described above, the present inventor developed a method for producing a dental filler by mixing a silica sol, an aqueous solution of silicic acid and an aqueous solution of a zirconium salt, drying the mixture solution with a spray drier, and then calcining the dried mixture, and they filed a patent application for this method (Refer to Patent document 3). With this invention, it is possible to obtain a dental filler in which the silica component originated from the silicic acid and the acidic zirconium component are well mixed with each other, and therefore properties of the aggregated particles obtained (such as the refractive index) are close to those of silica particles originated from the silica sol. However, even in this dental filler, as the silica particles originated from the silica sol are still mixed therein, the problems as described above have not completely been solved yet.

Furthermore, for solving the problems relating to the conventional type of dental fillers as described above, the present inventors developed a dental filler containing microparticles of a crystalline inorganic oxide comprising a zirconium silicate compound, and they filed a patent application for this dental filler (Refer to Patent document 4). This dental filler has excellent properties such as the strength or hardness substantially equivalent to those of natural teeth, or high resistance against abrasion as caused by teething. However, when the dental filler is used in some specific applications, the microparticles of the crystalline inorganic oxide are required to subject to a surface treatment with an organic metal oxide such as an organic silicon compound, an organic titanium compound, an organic zirconium compound or the like. However, because the microparticles of the crystalline inorganic oxide have a surface property for crystalline particles, it is not always easy to homogeneously treat the surface with the organic metal compound.

Under the circumstances, the present inventors have made strenuous research and development efforts for solving the problems as described above, and found that microparticles of amorphous inorganic oxide prepared by covering surfaces of silica-based fine particles with a composite metal oxide have the excellent properties as a dental filler, and they completed the present invention.

Patent document 1: JP H07-196428
Patent document 2: JP 2003-512406 (WO 01/030306)
Patent document 3: JP 2003-146822
Patent document 4: Japanese Patent Application No. 2006-086800

DISCLOSURE OF THE INVENTION

Problems to be Solved by the Invention

As described above, dental composite materials used in dental treatment are required to have, in addition to such properties as non-toxicity and insolubility, a sufficient strength or hardness equivalent to those of natural teeth, a sufficient resistance against abrasion as caused by teething, a surface smoothness after polishing by a dentist, an appropriate refractive index for giving the transparency equivalent to that of natural teeth, a color tone or a glazing property equivalent to those of natural teeth, and an X-ray radiopacity enabling differentiation of a treated or repaired portion from natural teeth during or after the dental treatment by a dentist, and most of the properties largely depend on the physical properties of a dental filler used when producing the dental composite material.

The present invention relates to a novel dental filler comprising microparticles of amorphous inorganic oxide satisfying the requirements to the dental filler as described above and making it possible to easily treat surfaces of such microparticles with an organic metal compound. More specifically, an object of the present invention is to provide a dental filler comprising microparticles of amorphous inorganic oxide, namely dried particles or calcined particles of amorphous inorganic oxide obtained by covering the surfaces of silica-based fine particles with a composite metal oxide, a method for producing the dental filler, and a dental composite material using the dental filler as described above.

Means for Solving the Problems

The present invention provides a dental filler comprising microparticles of amorphous inorganic oxide constituted by at least silica-based fine particles covered with a composite oxide comprising zirconium, silicon and oxygen.

The silica-based fine particles preferably have an average particle diameter in the range from 2 to 300 nm.

The microparticles of amorphous inorganic oxide are preferably selected from dried particles or calcined particles of the amorphous inorganic oxide constituted by at least the silica-based fine particles covered with a composite oxide comprising zirconium, silicon and oxygen.

The dried particles are preferably those having a form with a chain or network structure formed by the silica-based fine particles covered with the composite oxide comprising zirconium, silicon and oxygen, and a zonal substance or substances of the composite oxide having the same components as described above, extended or bridged between or among the silica-based fine particles covered with the above composite oxide, or those having a form with a massive structure formed by entwining or coagulating the above materials of the amorphous inorganic oxide with a chain or network structure, or those having a form with a grain-like structure formed by crushing the above materials of the amorphous inorganic oxide having a form with a chain or network structure or a massive structure.

The calcined particles are preferably those obtained by calcining the dried particles of the amorphous inorganic oxide, or those obtained by crushing thus calcined particles.

The microparticles of amorphous inorganic oxide are preferably those having been subjected to a surface treatment with one or more organic metal compounds selected from the group consisting of an organic silicon compound, an organic titanium compound and an organic zirconium compound.

The dental filler has a refractive index preferably in the range from 1.43 to 1.65.

The present invention provides a method for producing a dental filler comprising dried particles of amorphous inorganic oxide having a form with a chain or network structure formed by the silica-based fine particles covered with the composite oxide comprising zirconium, silicon and oxygen, and a zonal substance or substances of the composite oxide having the same components as described above, extended or bridged between or among the silica-based fine particles covered with the above composite oxide, or dried particles of amorphous inorganic oxide having a form with a massive structure formed by entwining or coagulating the above materials of the amorphous inorganic oxide having a form with a chain or network structure, which comprises the steps of:

(a) adding an alkali metal hydroxide and hydrogen peroxide into an aqueous solution in which a hydrate of zirconium oxide is suspended, and agitating the mixture solution to prepare a mixture aqueous solution in which the hydrate of zirconium oxide is peptized and dissolved;

(b) adding, with agitation, the mixture aqueous solution obtained in the step (a) and an aqueous solution of silicic acid into a silica sol in which silica-based fine particles with an average particle diameter in the range from 2 to 300 nm are dispersed in water;

(c) treating the mixture aqueous solution obtained in the step (b) above with a cation-exchange resin to remove an alkali metal component contained therein;

(d) putting the mixture aqueous solution obtained in the step (c) above in a reaction vessel, and subjecting the mixture aqueous solution to a hydrothermal treatment at a temperature in the range from 100 to 350° C., to prepare a mixture aqueous solution in which microparticles of amorphous inorganic oxide having a form with a chain or network structure are contained; and (e) drying the microparticles of the amorphous inorganic oxide contained in the mixture aqueous solution obtained in the step (d) above, to obtain dried particles of the amorphous inorganic oxide having a form with a chain or network structure or a massive structure.

The hydrate of zirconium oxide used in the step (a) above is preferably prepared by adding, with agitation, ammonium or ammonia water into an aqueous solution of one or more zirconates selected from the group consisting of zirconium oxychloride, zirconium oxysulfate, zirconium oxynitrate, zirconium oxyacetate, zirconium oxycarbonate and ammonium zirconium oxycarbonate, to obtain a neutralized reaction product, and then by washing the product with water.

The alkali metal hydroxide used in the step (a) above is preferably potassium hydroxide.

The aqueous solution of silicic acid used in the step (b) above is preferably prepared by diluting water glass with water and by treating the diluted water glass with a cation-exchange resin to remove an alkali metal component contained therein.

In the step (b) above, the silica sol is preferably heated to a temperature in the range from 70 to 95° C., before the mixture aqueous solution obtained in the step (a) above and the aqueous solution of silicic acid are added thereto.

The treatment for removing the alkali metal component contained in the step (c) above is carried out, so that pH of the mixture aqueous solution is adjusted to in the range from 7.0 to 10.0.

The operation, in the step (b) above, for adding the mixture aqueous solution obtained in the step (a) and the aqueous solution of silicic acid, and the operation, in the step (c) above, for removing the alkali metal component are preferably carried out in repetition several times.

The hydrothermal treatment in the step (d) above is preferably carried out in an autoclave for 10 to 100 hours.

The operation for drying in the step (e) is preferably carried out by using a hot air drier or a spray drier.

The dried particles of the amorphous inorganic oxide having a form with a chain or network structure or a massive structure obtained in the step (e) above are preferably calcined at a temperature in the range from 300 to 900° C. to obtain calcined particles of the amorphous inorganic oxide, with or without crushing the dried particles.

The microparticles of the amorphous inorganic oxide are preferably subjected to a surface treatment by adding one or more organic metal compounds selected from the group consisting of an organic silicon compound, an organic titanium compound and an organic zirconium compound into a solution of water and/or an organic solvent in which the dried particles or the calcined particles of the amorphous inorganic oxide are suspended, and then by hydrolyzing the organic metal compounds as described above.

The present invention provides a dental composite material containing the dental filler as described above and a hardenable resin.

The hardenable resin is preferably one or more resins selected from an acrylic resin, a methacrylic resin, an epoxy resin, a vinyl resin and a urethane resin.

The dental composite material is preferably used for one or more applications selected from the group consisting of dental restoratives, dental adhesives, dental mill blanks, dental cements, artificial dentures, dental corrective devices, adhesive agents for a dental correction, a dental casting or a dental coating.

EFFECTS OF THE INVENTION

The dental filler according to the present invention is a novel dental material having the properties as described below.

1) The dental filler substantially comprising microparticles of amorphous inorganic oxide according to the present invention have a refractive index in the range from 1.45 to 1.63, and more specifically in the range from 1.49 to 1.60, and therefore the dental filler can advantageously be used as a dental material. Furthermore, because the microparticles as the dental filler are selected from the dried particles or the calcined particles of the amorphous inorganic oxide constituted by at least the silica-based fine particles covered with a composite oxide comprising zirconium, silicon and oxygen, the surfaces of the microparticles can easily be treated with an organic metal compound such as an organic silicon compound, an organic titanium compound and an organic zirconium compound. Therefore, when it is required to adjust the refractive index of the microparticles as the dental filler, the refractive index can easily be adjusted to the range from 1.43 to 1.65 by such surface treatment as described above, and as a result, it is possible to easily obtain a dental filler having a refractive index well matched to the refractive index of a hardenable resin which will be used for preparation of a dental composite material.

2) Because both the dried particles and the calcined particles of the amorphous inorganic oxide as described above has the color tone which is white or milky white, the compatibility in the color tone with that of natural teeth is excellent. Furthermore, because the microparticles of the amorphous inorganic oxide are covered with a composite oxide containing zirconium, the microparticles as the dental filler have a sufficient level of X-ray radiopacity by which differentiation of the treated or repaired portion of a tooth from the tooth tissue of natural teeth is distinguishable based on an X-ray photograph taken during or after the dental treatment by a dentist.

3) The calcined particles of the amorphous inorganic oxide are a little inferior to the microparticles of crystalline inorganic oxide comprising a zirconium silicate compound as descried in Patent document 4 in such physical properties as the mechanical strength and the abrasion resistance, but the mechanical strength and the abrasion resistance of the calcined particles are sufficient to be used as a dental material. However, the mechanical strength and the abrasion resistance of the dried particles of amorphous inorganic oxide are not sufficient as compared to those of the calcined particles, and therefore the dried particles are preferable to use in applications not requiring a high mechanical strength and a high abrasion resistance thereof.

4) The dried particles or the calcined particles of amorphous inorganic oxide as described above can be used for preparation of a dental composite material as they are, although the circumstances vary dependent upon such parameters as a type of the hardenable resin used when the dental composite material is prepared. However, when it is necessary to further improve the dispersibility in or the adhesiveness to the hardenable resin, such properties can be improved by subjecting the microparticles of amorphous inorganic oxide to a surface treatment with the organic metal compound as described above.

5) Because the microparticles of amorphous inorganic oxide are composed of extremely stable materials, the materials are not soluble in saliva or any liquids drunk from a mouth even when the microparticles are used as a dental material, and also, because the microparticles do not contain any material of toxic heavy metal oxides at all, they never give any negative effect to a human body.

Furthermore, the method according to the present invention relates to a novel method for producing a dental filler, and the method makes it possible to easily produce a dental filler comprising the microparticles of amorphous inorganic oxide constituted by at least silica-based fine particles covered with a composite oxide comprising zirconium, silicon and oxygen. Furthermore, with the method according to the present invention, it is possible to obtain the dried particles or the calcined particles of amorphous inorganic oxide having a specific form with a chain or network structure or a massive structure (including a spherical structure), and also the crushed particles thereof having a form with a grain-like structure.

Furthermore, because the dental composite material according to the present invention has the optical and mechanical properties satisfying the requirements to a dental material as described above, the material is extremely effective as various types of the materials to be used in the field of dental medical treatment at present and in the future.

BEST MODE FOR CARRYING OUT THE INVENTION

A dental filler, a method for producing the dental filler, and a dental composite material using the dental filler according to the present invention are described below in detail.
[Dental Filler and a Method for Producing the Dental Filler]
Dental Filler The dental filler according to the present invention comprises microparticles of amorphous inorganic oxide constituted by at least silica-based fine particles covered with a composite oxide comprising zirconium, silicon and oxygen, which are prepared by covering the surface of silica-based fine particles with the composite oxide as described above.

The silica-based fine particles preferably have an average particle diameter in the range from 2 to 300 nm. When the average particle diameter is less than 2 nm, mechanical strength of the dental filler produced by using such silica-based fine particles, especially the compression strength and the bending strength become lower. When the average particle diameter is over 300 nm, the smoothness and glazing property at a polished surface of the tooth repaired with use of a dental composite material which contains a dental filler produced by using such silica-based fine particles are insufficient, which is not preferable.

The composite oxide used for covering the surfaces of the silica-based fine particles comprises zirconium, silicon and oxygen, and the constitutional formula in a part is as shown below:

(I)

Furthermore, the composite oxide may further contain titanium or aluminum in addition to the above components, and the constitutional formulae in a part are as shown below:

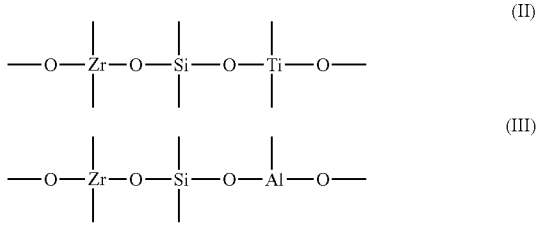

(II)

(III)

The microparticles of amorphous inorganic oxide are selected from dried particles or calcined particles of the amorphous inorganic oxide constituted by at least silica-based fine particles covered with a composite oxide comprising zirconium, silicon and oxygen.

The dried particles are also selected from (1) those having a form with a chain or network structure formed by the silica-based fine particles covered with the composite oxide comprising zirconium, silicon and oxygen, and a zonal substance or substances of the composite oxide having the same components as described above, extended or bridged between or among the silica-based fine particles covered with the above composite oxide, or (2) those having a form with a massive structure formed by entwining or coagulating the above materials of the amorphous inorganic oxide with a chain or network structure, or (3) those having a form with a grain-like structure formed by crushing the above materials of the amorphous inorganic oxide with a chain or network structure or a massive structure.

Of these dried particles, the above particles (1) having a form with a chain or network structure are as shown in FIG. 1 indicating a photograph taken by an electron microscope, and also the above particles (2) having a form with a massive structure are as shown in FIG. 2 indicating a photograph taken by the same.

However, when a spray drier is used for the drying, the dried particles are also formed by entwining or coagulating the above materials of the amorphous inorganic oxide with a chain or network structure, and have a form with a spherical structure. Therefore, the term of "a massive structure" used in the present invention includes a spherical structure.

The calcined particles are selected from those obtained by calcining the dried particles of the amorphous inorganic oxide as described above, or those obtained by crushing thus calcined particles. Furthermore, the calcined particles have almost the same form as that of the dried particles as described above, but the crushed ones have a form with a grain-like structure.

Because the dried particles are not sufficient in the mechanical strength and the abrasion resistance, it is generally desirable to use the calcined particles. Accordingly, the dried particles and the calcined particles are preferably used for different applications.

Furthermore, the microparticles of amorphous inorganic oxide are preferably selected from those having been subjected to a surface treatment with one or more organic metal compounds selected from the group consisting of an organic silicon compound, an organic titanium compound and an organic zirconium compound. By subjecting the microparticles of the amorphous inorganic oxide to the surface treatment, it is possible to easily obtain the microparticles having a refractive index compatible with that of the hardenable resin to be used when a dental composite material is prepared, and also the microparticles having an improved dispersibility in and adhesiveness to the hardenable resin can be obtained.

In both cases of the dried particles and the calcined particles, surfaces of the microparticles of amorphous inorganic oxide according to the present invention can easily be treated with the above organic metal compounds, and therefore it is possible to easily obtain a dental filler comprising the above microparticles having surface properties (such as a refractive index) desired by various manufacturers of dental composite materials who may use different types of hardenable resins.

The organic silicon compound includes, but not limited to, the silicon compound expressed by the following general formula (1):

$$R_n SiX_{4-n} \tag{1}$$

(wherein R denotes an unsubstituted or substituted hydrocarbon group having 1 to 10 carbon atoms, the hydrocarbon group of which may be identical or different from each other; and X denotes an alkoxy group having 1 to 4 carbon atoms, a silanol group, a halogen group or hydrogen; and n is an integer of 0 to 3).

More specifically, the organic silicon compound includes, but not limited to, methyl trimethoxysilane, dimethyl dimethoxysilane, phenyl trimethoxysilane, diphenyl dimethoxysilane, methyl triethoxysilane, dimethyl diethoxysilane, phenyl triethoxysilane, diphenyl diethoxysilane, isobutyl trimethoxysilane, vinyl trimethoxysilane, vinyl triethoxysilane, vinyl-tris(β methoxyethoxysilane) silane, 3,3,3-trifluoropropyl trimethoxysilane, methyl-3,3,3-trifluoropropyl dimethoxysilane, β-(3,4 epoxycyclohexyl) ethyl trimethoxysilane, γ-glycidoxytripropyl trimethoxysilane, γ-glycidoxypropylmethyl diethoxysilane, γ-glycidoxypropyl triethoxysilane, γ-methacryloxypropylmethyl dimethoxysilane, γ-methacryloxypropyl trimethoxysilane, γ-methacryloxypropylmethyl diethoxysilane, γ-methacryloxypropyl triethoxysilane, N-β(aminoethyl) γ-aminopropylmetyl dimethoxysilane, N-β(aminoethyl) γ-aminopropyl trimethoxysilane, N-β(aminoethyl) γ-aminopropyl triethoxysilane, γ-aminopropyl trimethoxysilane, γ-aminopropyl triethoxysilane, N-phenyl-γ-aminopropyl trimethoxysilane, γ-mercaptopropyl trimethoxysilane, trimethylsilanol, methyl trichlorosilane, methyl dichlorosilane, dimethyl dichlorosilane, trimethyl chlorosilane, phenyl trichlorosilane, diphenyl dichlorosilane, vinyl trichlorosilane, trimethyl bromosilane, and diethylsilane. Of these materials, it is preferable to use vinyl trimethoxysilane, vinyl triethoxysilane, γ-methacryloxypropylmethyl dimethoxysilane, γ-methacryloxypropyl trimethoxysilane, γ-methacryloxypropyl methyl diethoxysilane, γ-methacryloxypropyl triethoxysilane, which are often used as a silane coupling agent, or a mixture thereof.

The organic titanium compound includes, but not limited to, tetramethyl titanate, tetraisopropyl titanate, tetra n-butyl titanate, butyl titanate dimmer, and tetra (2-ethylhexyl) titanate. The organic zirconium compound includes, but not limited to, zirconium isopropoxyde, zirconium n-butoxyde, zirconium acetylacetonate, and zirconyl acetate.

Furthermore, if required, the surface treatment may be carried out with an organic aluminum compound such as aluminum acetyl acetonate and chelate compound of organic acid salt of aluminum.

The surface treatment with the organic metal compound may be performed with a mixture of the organic metal compounds, and furthermore may be carried out several times with the same organic metal compound, or with different types of organic metal compounds.

A thickness of the organic metal oxide (or a hydrolyzate thereof in a case of an organic silicon compound containing silane, an organic titanium compound, or an organic zirconium compound) bonded to or covering surfaces of the microparticles of amorphous inorganic oxide is 300 nm or below, and preferably 100 nm or below, although the thickness varies dependent upon a type of the organic metal compound used in the surface treatment, or a desired value to a refractive index, dispersibility or other properties of the microparticles to be obtained. When the thickness is over 300 nm, some of the organic metal compound not fully hydrolyzed during the surface treatment and having the hydrosis group remained, and/or some of the products reacted between the organic metal compounds themselves without having reacted with or adhered to the surfaces of the microparticles may exist in the layer formed on the surfaces of the microparticles, thereby the stability of the particle surface being degraded with a time elapse, and when such microparticles are dispersed in a hardenable resin, the microparticles may adhere to each other or may aggregate, which is not preferable.

A refractive index of the microparticles of amorphous inorganic oxide obtained as described above is in the range from 1.43 to 1.65, preferably in the range from 1.45 to 1.63, although the value varies on whether the microparticles are subjected to the surface treatment or dependent upon a type of the organic metal compound used in the surface treatment or a thickness of the layer achieved through the surface treatment. When the refractive index is less than 1.43, because the value is lower than a refractive index of the hardenable resin, a degree of light scattering inside the microparticles increases, and because it makes a cause of whitening, the desired beauty would not be obtained. When the refractive index is over 1.65, because the value is higher than a refractive index of the hardenable resin, a degree of light scattering inside the microparticles increases also in this case, and because it makes a cause of whitening, the desired beauty would not be obtained.

Therefore, it is preferable that the dental filler comprising the microparticles of amorphous inorganic oxide also has a refractive index in the range from 1.43 to 1.65, and more preferably in the range from 1.45 to 1.63.

Furthermore, although the refractive index of the microparticles of amorphous inorganic oxide which are not subjected to the surface treatment varies dependent upon the composition thereof and/or the conditions for their preparation, it is preferable to be in the range from 1.45 to 1.63, more preferably in the range from 1.49 to 1.60, and most preferably in the range from 1.53 to 1.57.

Whether or not the surface treatment is performed, it is preferable to use the microparticles of amorphous inorganic oxide having an average particle diameter in the range from 2 to 50000 nm, more preferably in the range from 7 to 5000 nm, and most preferably in the range from 10 to 500 nm. When the average particle diameter is less than 2 nm, a mechanical strength, especially a compression strength or a bending strength of the dental filler comprising the microparticles as described above becomes lower. When the average particle diameter is over 50000 nm, sometime it becomes difficult to polish a treated or repaired portion of a tooth obtained by hardening a dental composite material which is prepared with the dental filler, and if the treated or repaired portion is polished by a dentist, the surface thereof would not have a sufficient smoothness or glazing property as described above, which is not preferable.

When the microparticles of amorphous inorganic oxide are used as a dental filler, it is preferable to use them alone, but the microparticles may be used together with other particles of inorganic oxide to be mixed, which are generally used as constituents of the dental filler, such as silica particles or zirconium oxide particles. There is no specific restriction over a mixing amount of such conventional particles, but the mixing ratio thereof is not more than 70% by weight, preferably not more than 50% by weight, and more preferably not more than 30% by weight to the total amount of the dental filler.

A method for producing the dental filler according to the present invention is described below, but it should be noted that the dental filler according to the present invention is not limited to that obtained by the method as described below.

Method for Producing a Dental Filler

The method according to the present invention is employed for producing a dental filler comprising dried particles of amorphous inorganic oxide having a form with a chain or network structure formed by the silica-based fine particles covered with the composite oxide comprising zirconium, silicon and oxygen, and a zonal substance or substances of the composite oxide having the same components as described above, extended or bridged between or among the silica-based fine particles covered with the above composite oxide, or dried particles of amorphous inorganic oxide having a form with a massive structure formed by entwining or coagulating the above materials of the amorphous inorganic oxide having a form with a chain or network structure, which comprises the steps of:

(a) adding an alkali metal hydroxide and hydrogen peroxide into an aqueous solution in which a hydrate of zirconium oxide is suspended, and agitating the mixture solution to prepare a mixture aqueous solution in which the hydrate of zirconium oxide is peptized and dissolved;

(b) adding, with agitation, the mixture aqueous solution obtained in the step (a) and an aqueous solution of silicic acid into a silica sol in which silica-based fine particles with an average particle diameter in the range from 2 to 300 nm are dispersed in water;

(c) treating the mixture aqueous solution obtained in the step (b) above with a cation-exchange resin to remove an alkali metal component contained therein;

(d) putting the mixture aqueous solution obtained in the step (c) above in a reaction vessel, and subjecting the mixture aqueous solution to a hydrothermal treatment at a temperature in the range from 100 to 350° C., to prepare a mixture aqueous solution in which microparticles of amorphous inorganic oxide having a form with a chain or network structure are contained; and (e) drying the microparticles of the amorphous inorganic oxide contained in the mixture aqueous solution obtained in the step (d) above, to obtain dried particles of the amorphous inorganic oxide having a form with a chain or network structure or a massive structure.

Each of the steps is described below in detail.

Step (a)

The hydrate of zirconium oxide (sometimes referred to simply as "the zirconium oxide hydrate" hereinafter) to be used in the present invention is expressed by the chemical formula of $ZrO_2.xH_2O$, and also zirconium hydroxide ($Zr(OH)_n$) is included in the category of the zirconium oxide hydrate.

It is generally known that the hydrate of zirconium oxide is dissolved in an acid or in an aqueous solution containing an acid, but is little dissolved in an aqueous solution containing water or containing water and an alkali component.

Therefore, in the step (a), a suspended aqueous solution is prepared by suspending zirconium hydroxide in pure water or distilled water. Then, a hydroxide of an alkali metal such as potassium and sodium (namely, potassium hydroxide, sodium hydroxide and the like) and hydrogen peroxide are added into the suspended aqueous solution as described above with agitation, thereby the zirconium hydroxide being hydrated, and thus obtained zirconium oxide hydrate is peptized and dissolved in the mixture aqueous solution (hereinafter referred to as "the mixture aqueous solution (1)"). In this case, it is preferable to use potassium hydroxide as the alkali metal hydroxide, because when using the potassium hydroxide, the peptization easily occurs as compared to the sodium hydroxide.

The alkali metal hydroxide ($M_2O$) is preferably added into the suspended aqueous solution at the molar ratio ($M_2O/ZrO_2 \cdot xH_2O$) against the zirconium oxide hydrate ($ZrO_2 \cdot xH_2O$) in the range from 1/1 to 10/1, and preferably in the range from 2/1 to 5/1. When the molar ratio is less than 1/1, the peptization of the zirconium oxide hydrate does not proceed smoothly. When the molar ratio is over 10/1, the peptization proceeds quickly, but, because an excessive quantity of alkali metal ions is contained in the aqueous solution, the alkali metal ions are required to remove in the subsequent step with use of a cation-exchange resin, which is not preferable from the economical point of view.

The hydrogen peroxide ($H_2O_2$) is added into the suspended aqueous solution preferably at the molar ratio ($H_2O_2/ZrO_2 \cdot xH_2O$) against the zirconium oxide hydrate ($ZrO_2 \cdot xH_2O$) in the range from 5/1 to 30/1, and preferably in the range from 10/1 to 25/1. When the molar ratio is less than 5/1, the peptization of the zirconium oxide hydrate does not proceed well. When the molar ratio is over 30/1, the peptization proceeds quickly and a time required for dissolution becomes shorter, but a large amount of hydrogen peroxide not reacted yet remains in the aqueous solution, which is not preferable from the economical point of view.

Furthermore, the hydrogen peroxide is preferably added as an aqueous solution of hydrogen peroxide with a concentration in the range from 18 to 35% by weight.

The hydrate of zirconium oxide can be prepared by a known conventional method, for instance, by hydrolyzing a zirconium salt in an aqueous solution, or by adding an alkali metal component or ammonia in the aqueous solution to cause a neutralization reaction. In the present invention, however, it is preferable to use a neutralized reaction product (i.e., a hydrate of zirconium oxide) obtained by adding, with agitation, ammonia or ammonia solution into an aqueous solution in which one or more zirconates selected from the group consisting of zirconium oxychloride ($ZrOCl_2 \cdot xH_2O$), zirconium oxysulfate ($ZrOSO_4 \cdot xH_2O$), zirconium oxynitrate ($ZrO(NO_3)_2 \cdot xH_2O$), zirconium oxyacetate ($ZrO(C_2H_3O_2)_2$), zirconium oxycarbonate ($ZrOCO_3 \cdot xH_2O$) and ammonium zirconium oxycarbonate (($NH_4)_2ZrO(CO_3)_2$) are dissolved in pure water or distilled water, to cause a neutralization reaction, and then washing thus obtained product by pure water or distilled water sufficiently.

As the zirconate, it is preferable to use zirconium oxychloride ($ZrOCl_2 \cdot 8H_2O$). It should be noted that the zirconium oxychloride, the zirconium oxysulfate, the zirconium oxynitrate, the zirconium oxyacetate, and the zirconium oxycarbonate as described above are sometimes also referred to as zirconyl chlorate, zirconyl sulfate, zirconyl nitrate, zirconyl acetate, and zirconyl carbonate respectively.

Furthermore, in place of the zirconate as described above, it is possible to use one or more zirconates selected from the group consisting of zirconium carbonate ($ZrCO_4 \cdot ZrO_2 \cdot xH_2O$), zirconium sulfate ($Zr(SO_4)_2 \cdot xH_2O$), zirconium chloride ($ZrCl_2$, $ZrCl_3$, or $ZrCl_4$), and zirconium nitrate ($Zr(NO_3)_4 \cdot xH_2O$).

A content of the above zirconate in the aqueous solution is in the range from 10 to 20% by weight, and preferably in the range from 13 to 17% by weight.

It is preferable to add the ammonia ($NH_3$) or ammonia water ($NH_4OH$) into the aqueous solution at the molar ratio ($NH_3/ZrOX_n$ or $NH_4OH/ZrOX_n$) against the zirconate ($ZrOX_n$) in the range from 13/7 to 13/2, and more preferably in the range from 13/5 to 13/4. When the molar ratio is less than 13/7, the zirconate is not neutralized sufficiently, thereby a part of the zirconate being remained in the aqueous solution. When the molar ratio is over 13/2, an amount of ammonia is excessive, and a long time is required for washing off the residual ammonia, which is not preferable.

Furthermore, it is preferable that the ammonia water contains ammonia with a concentration in the range from 5 to 15% by weight.

The neutralization reaction is preferably performed at a temperature in the range from 5 to 20° C., and more preferably in the range from 10 to 15° C. When the temperature is over 20° C., some zirconium compounds other than the zirconium oxide hydrate (such as a dimer of the zirconium oxide hydrate and the like) may be produced by neutralization of the zirconate under such a condition, which is not preferable.

It is necessary to sufficiently wash the hydrate of zirconium oxide obtained from the neutralization reaction and then separated by filtration with pure water or distilled water for removing unreacted materials (such as $ZrOX_n$ or the like) or byproducts ($NH_4X$ and the like) from the neutralization reaction as much as possible.

A content of zirconium components (i.e., a peptized product of the zirconium oxide hydrate) dissolved and contained in the mixture aqueous solution obtained as described above is desirably in the range from 0.3 to 5% by weight in terms of $ZrO_2$, although there is no specific restriction over the value.

Step (b)

In the step (b), the mixture aqueous solution (1) obtained in the step (a) and an aqueous solution of silicic acid are added respectively with agitation into a silica sol in which silica-based fine particles with an average particle diameter in the range from 2 to 300 nm are dispersed in water.

As the silica sol, any one procurable from the market (such as S1-30 produced by JGC Catalysts and Chemicals Ltd.) may be used on the condition that the product contains silica-based fine particles with an average particle diameter in the range from 2 to 300 nm. When the average particle diameter is less than 2 nm, the mechanical properties, especially the compression strength or bending strength of the dental filler produced by using such silica-based fine particles become lower. When the average particle diameter is over 300 nm, the smoothness and glazing property at a polished surface of the tooth repaired with use of a dental composite material which contains a dental filler comprising the microparticles of amorphous inorganic oxide produced by using such silica-based fine particles become insufficient, which is not preferable. It should be noted that the average particle diameter as described above indicates a value measured by a laser diffraction scattering method.

A content of the silica-based fine particles contained in the silica sol is preferably in the range from 0.5 to 5% by weight. When the content is less than 0.5% by weight, it becomes difficult to economically obtain the microparticles of amorphous inorganic oxide as described above. When the content is over 5% by weight, the mixture solution obtained by adding the mixture aqueous solution (1) and the aqueous solution of silicic acid into such silica sol becomes unstable with aggregation of the silica-based fine particles, which disadvantageously makes it difficult to obtain the microparticles of amorphous inorganic oxide having a form with a chain or network structure.

Furthermore, a content of the zirconium components contained in the mixture aqueous solution (1) is preferably adjusted to the range from 0.3 to 5% by weight, and more preferably in the range from 0.5 to 3% by weight in terms of $ZrO_2$ before adding to the silica sol, although the value varies dependent upon a content of the silica-based fine particles contained in the silica sol, a content of silicic acid contained in the aqueous solution and the properties thereof to be added in this step. When the content is less than 0.3% by weight, it becomes difficult to economically obtain the microparticles of amorphous inorganic oxide as described above. When the content is over 5% by weight, stability of the mixture aqueous solution after having been added to the silica sol is low, and in addition viscosity of the mixture aqueous solution is apt to become higher, which is not preferable.

On the other hand, the aqueous solution of silicic acid (sometimes hereinafter referred to as "silicic acid solution"), which is used in this step, is preferably prepared by treating an aqueous solution of a silicate such as an alkali metal silicate, or an organic base silicate with a cation-exchange resin added in the solution, and by removing the cation-exchange resin thereafter. The silicates include, but not limited to, alkali metal silicates such as sodium silicate (water glass), and potassium silicate and organic base silicates such as a quaternary ammonium silicate.

pH of the silicic acid solution is preferably in the range from 2 to 4, and more preferably in the range from 2 to 3. A content of silicon components is preferably in the range from 0.5 to 5% by weight, and more preferably in the range from 3 to 4% by weight in terms of $SiO_2$. When the pH is less than 2, a great amount of the cation-exchange resin is necessary for the treatment and the time required for the processing becomes longer, which is not preferable from the economical point of view. When the pH is over 4, the degree of removing the alkali metal component contained therein is low, and stability of the obtained solution is deteriorated, which is not preferable. Furthermore, when the content is less than 0.5% by weight, it becomes difficult to economically obtain the microparticles of amorphous inorganic oxide as described above. When the content is over 5% by weight, stability of the silicic acid solution is disadvantageously low.

It is preferable that the aqueous solution of the silicic acid satisfying the requirements as described above is produced by diluting water glass (i.e., sodium silicate) with water and then by treating the diluted water glass with a cation-exchange resin to remove the alkali metal component contained therein.

When the zirconium components contained in the mixture aqueous solution (1) are expressed as $ZrO_2$ (i.e., in terms of $ZrO_2$) and the silicon components contained in the aqueous solution of silicic acid are expressed as $SiO_2$-(1) (i.e., in terms of $SiO_2$), the molar ratio ($ZrO_2/SiO_2$-(1)) of the zirconium components against the silicon components contained in such solutions as described above is preferably adjusted in advance to in the range 1/16 to 1/1 and more preferably in the range from 1/8 to 1/2. Thereafter, each of the mixture aqueous solution (1) and the aqueous solution of silicic acid thus adjusted are gradually added to the silica sol. When the molar ratio is less than 1/16, it becomes difficult to obtain the microparticles of amorphous inorganic oxide with a chain or network structure. When the molar ratio is over 1/1, the aqueous solution mixed becomes unstable during addition to the silica sol with aggregation of the silica-based fine particles, which is not preferable.

When the silica-based fine particles contained in the silica sol are expressed as $SiO_2$-(2) (i.e., in terms of $SiO_2$), the weight ratio $\{(ZrO_2+SiO_2\text{-}(1))/SiO_2\text{-}(2)\}$ of the zirconium components and the silicon components against the silica-based fine particles contained in such solutions as described above is preferable to be in the range from 7/100 to 15/10, and more preferably in the range from 5/10 to 1/1, although the value varies dependent upon a degree required for covering a composite oxide as described below on the silica-based fine particles contained in the silica sol. When the weight ratio is less than 7/100, it becomes difficult to obtain the microparticles of amorphous inorganic oxide with a chain or network structure. When the weight ratio is over 15/10, the mixture solution becomes unstable during addition to the silica sol with aggregation of the silica-based fine particles, which is not preferable The silica sol is preferably heated to a temperature in the range from 70 to 95° C., and more preferably in the range from 80 to 90° C. before the mixture aqueous solution (1) and the aqueous solution of silicic acid are added thereto. When the temperature is less than 70° C., the hydrolysis reactions of the zirconium components and the silicon components as described above do not proceed sufficiently, and when the temperature is over 95° C., water in the silica sol may be evaporated, which is not preferable. The mixture aqueous solution (1) and the aqueous solution of silicic acid may be also heated before they are added to the silica sol, but can be used without heating.

Addition of the mixture aqueous solution (1) and the aqueous solution of silicic acid is preferably carried out gradually over 4 to 24 hours, although the required time for the addition varies dependent upon each content of the above components or each quantity (or total quantity) thereof to be added.

When the mixture aqueous solution (1) and the aqueous solution of silicic acid are added with agitation into the silica sol as described above, the hydrolysis reactions of the zirconium components and the silicon components occurs in the mixture aqueous solution (hereinafter referred to as "mixture aqueous solution (2)"), and surfaces of the silica-based fine particles contained in the silica sol are covered with partial hydrolyzate or hydrolyzate of the above components.

With addition of the mixture aqueous solution (1) having high alkalinity to the silica sol, pH of the mixture aqueous solution (2) becomes higher. Therefore, it is preferable to stop the addition of the mixture aqueous solution (1) and also the aqueous solution of silicic acid, when the pH of the mixture aqueous solution (2) reaches to 11, or more preferably to 10.5. When the pH is over 11, the silica-based fine particles contained in the silica sol start to be dissolved from their surfaces by the high alkalinity based on the alkali metal component contained in the mixture aqueous solution (2), which is not preferable.

Therefore, if the addition of the mixture aqueous solution (1) and the aqueous solution of silicic acid has not been completed at the time of which the pH reached to about 11, it is preferable that the mixture aqueous solution (2) having pH of about 11 is subjected to the step (c) as described below to remove the alkali metal component contained therein, and thereafter the operation for the step (b) as described above is repeated again.

When it is required to cover surfaces of the silica-based fine particles with a composite oxide comprising titanium, aluminum or the like, an aqueous solution of a titanium compound having a hydrolytic property, such as tetramethyl titanate, tetraisopropyl titanate, tetra-n-butyl titanate, butyl titanate dimmer or tetra(2-ethylhexyl) titanate, or an aqueous solution of an aluminum compound having a hydrolytic property, such as sodium aluminate may be added, in addition to the mixture aqueous solution (1) containing the zirconium compounds and the aqueous solution of silicic acid containing the silicon components as described above.

Step (c)

In the step (c), the mixture aqueous solution (2) obtained in the step (b) is subjected to a treatment with a cation-exchange resin for removing an alkali metal component contained therein.

There is no specific restriction over the cation-exchange resin used in this step, but it is preferable to use the cation-exchange resin such as SK1BH which is a product as provided by Mitsubishi Chemicals Co.

In this step, it is preferable that the mixture aqueous solution (2) is subjected to the above treatment, until the time of which the pH of the mixture aqueous solution (2) reaches to a value in the range from 7.0 to 10.0 and more preferably to the range from 8.5 to 9.5. When the pH is less than 7.0, the mixture aqueous solution obtained becomes unstable with aggregation of the silica-based fine particles caused by which the alkali metal component is excessively removed. When the pH is over 10.0, the silica-based fine particles contained in the silica sol may be dissolved in a short time by the high alkalinity based on the alkali metal component, which will be brought when the addition of the mixture aqueous solution (1) and the aqueous solution of silicic acid is repeated as described above, which is not preferable.

When it is necessary to further add the mixture aqueous solution (1) and the aqueous solution of silicic acid solution into the mixture aqueous solution obtained in this step, the operations in the step (b) and in the step (c) may be repeated several times according to the necessity. When repetition of the operation in the step (b) is not necessary or has been completed, the mixture aqueous solution obtained (hereinafter referred to as "mixture aqueous solution (3)") is subjected to the operation in the step (d).

Step (d)

In this step (d), the mixture aqueous solution (3) obtained in the step (c) is put in a reaction vessel, and is subjected to a hydrothermal treatment at a temperature in the range from 100 to 350° C.

There is no specific restriction over the reaction vessel used in this step so long as the reaction vessel is a pressure-resistant and heat-resistant vessel capable of enduring a pressure in the range of 0.5 to 16.5 Mpa, but it is preferable to use an autoclave made from stainless steel.

The hydrothermal treatment is carried out preferably for 10 to 100 hours and more preferably for 20 to 40 hours at a temperature preferably in the range from 100 to 350° C., and more preferably in the range from 150 to 200° C. When the hydrothermal treatment is carried out at a temperature less than 100° C., the condensation reaction of partial hydrolyzate and/or hydrolyzate obtained from the hydrolysis reaction of the zirconium components and the silicon components contained therein does not proceed sufficiently, and it becomes difficult to obtain the microparticles of amorphous inorganic oxide having a form with a chain or network structure, which are constituted by at least silica-based fine particles covered with a composite oxide comprising zirconium, silicon and oxygen. When the hydrothermal treatment is carried out at a temperature over 350° C., a pressure-resistant vessel capable of enduring a pressure not less than 16.5 Mpa is required, which is not preferable from the economical point of view.

When the hydrothermal treatment is carried out for a period of time less than 10 hours, the condensation reaction as described above does not proceed sufficiently, and it becomes difficult to obtain the microparticles of amorphous inorganic oxide having a form with a chain or network structure as described above. Also, when the hydrothermal treatment is carried out for a period of time more than 100 hours, there is no positive effect over formation of the microparticles of amorphous inorganic oxide having a form with a chain or network structure as described above, which is not preferable from the economical point of view.

Thus, the mixture aqueous solution (hereinafter referred to as "mixture aqueous solution (4)") containing the microparticles of amorphous inorganic oxide having a form with a chain or network structure, which are constituted by at least silica-based fine particles covered with a composite oxide comprising zirconium, silicon and oxygen, is obtained.

However, the mixture aqueous solution (4) hardly contains the microparticles of amorphous inorganic oxide having a form with a massive structure or the like formed by entwining or aggregating the above materials of the amorphous inorganic oxide with a chain or network structure, although the situation varies dependent upon a concentration of the solid material contained in the mixture aqueous solution (4).

Step (e)

In the step (e), a solid material comprising the microparticles of amorphous inorganic oxide contained in the mixture aqueous solution (4) as described above is dried.

For drying the solid material as described above, any conventional method can be applied. More specifically, it can be dried through a drying process generally employed, namely by filtering the solid material from the mixture aqueous solution (4), washing the filtrated solid material with pure water or distilled water according to the necessity, and then drying the filtrated solid material at a temperature in the range from 100 to 200° C. with a conventional dryer using a hot air.

Furthermore, the solid material can be dried by condensing the mixture aqueous solution (4) to a concentration of 8 to 12% by weight with use of an ultra filtration unit using a membrane filter, and then drying the solid material contained in the condensed solution directly at a temperature in the range from 100 to 200° C. with a conventional dryer using a hot air.

However, to obtain the microparticles of amorphous inorganic oxide having the particle diameters being not widely ranged and with a narrow particle distribution, it is preferable to adjust a concentration of the solid material contained in the mixture aqueous solution (4) to the range from 0.01 to 10% by weight, preferably to the range from 0.07 to 5% by weight, and more preferably to the range from 0.1 to 3.0% by weight, and then spray-dry the obtained solution containing the solid material with use of a spray drier. When the concentration of the solid material is less than 0.01% by weight, a percentage of the particles with the diameter of 10 nm or less becomes higher and a yield of the product (i.e., the microparticles of amorphous inorganic oxide) becomes disadvantageously lower. Furthermore, when the solid material concentration is over 10% by weight, viscosity of the mixture aqueous solution becomes higher with a decrease of its stability, which makes it difficult to obtain the microparticles of amorphous inorganic oxide having the particle diameters being not widely ranged and with a narrow particle distribution. Furthermore, a percentage of particles having the diameter of 10000 nm or more becomes higher and sometimes large-size particles having the diameter over 50000 nm are formed, and if the particles are used as they are, as a dental filler without being crushed, sometimes it becomes difficult to polish a treated or repaired portion of the tooth by a dentist or the transparency at the treated or repaired portion becomes disadvantageously lower.

As the spray drier as described above, any known one (such as the disk rotation type or the nozzle type) may be used. The spray drying is performed according to the known method by spraying the concentrated mixture aqueous solution into a hot air stream for the spray drier.

In this step, a temperature of the hot air stream at the inlet for spraying the mixture aqueous solution is in the range from 150 to 200° C., and preferably in the range from 170 to 180° C. The temperature of the air stream at the outlet thereof is preferably in the range from 40 to 60° C. When the air temperature at the inlet is less than 150° C., the solid material contained in the sprayed mists would not be dried sufficiently. When the air temperature at the inlet is over 200° C., it is not preferable from the economical point of view. When the air temperature at the outlet is less than 40° C., the solid material contained in the sprayed mists would not be dried sufficiently and sometimes it will adhere to some places inside the spray drier, which is not preferable.

The microparticles of amorphous inorganic oxide obtained by spray-drying as described above have a form with a spherical structure or the like, and the particle diameters thereof are not widely ranged. With the method, it is also possible to easily obtain the microparticles of amorphous inorganic oxide having an average particle diameter in the range from 10 to 10000 nm.

It is needless to say, however, that the solid material contained in the mixture aqueous solution can be dried in any generally known drying device as described above at a temperature in the range from 100 to 200° C. In this case, however, because it is impossible to obtain the dried particles of amorphous inorganic oxide having the particle diameters being not widely ranged and sometimes a block of the particles is formed, it is necessary to adjust the particle diameters by crushing the dried particles with a pulverizer or a grinder such as a mortar and a bowl mill.

As described above, with the present invention, it is possible to obtain the dried particles of amorphous inorganic oxide having a form with a chain or network structure formed by the silica-based fine particles covered with the composite oxide comprising zirconium, silicon and oxygen, and a zonal substance or substances of the composite oxide having the same components as described above, extended or bridged between or among the silica-based fine particles covered with the above composite oxide, or the dried particles of amorphous inorganic oxide having a form with a massive structure (including a spherical structure) formed by entwining or coagulating the above materials of the amorphous inorganic oxide having a form with a chain or network structure, or the dried particles of amorphous inorganic oxide having a form with a grain-like structure formed by crushing the above materials of the amorphous inorganic oxide with a chain or network structure or a massive structure.

Calcining Step

In this step, the dried particles of amorphous inorganic oxide obtained in the step (e) are calcined at a temperature in the range from 300 to 900° C.

It is preferable to calcine the dried particles of the amorphous inorganic oxide in a quartz-made crucible placed in an electric furnace for one hour or more, preferably for 3 to 4 hours at a temperature in the range from 300 to 900° C., more preferably in the range from 500 to 800° C. When the temperature employed for the calcination is less than 300° C., it becomes impossible to obtain a desired mechanical strength of the calcined particles and also a desired refractive index thereof (which is in the range from 1.45 to 1.63), because the density of the covering material (i.e., the composite oxide as described above) does not become higher. As a result, sometimes a color tone of the tooth repaired with use of a dental composite material containing the calcined particles as a dental filler may not match with that of natural teeth. When the temperature employed for the calcination is over 900° C., sometimes crystallization of zirconium oxide ($ZrO_2$) occurs, which makes it impossible to obtain the desired mechanical strength of the calcined particles, and also the desired refractive index thereof as described above. As a result, sometimes a color tone of the tooth repaired with use of a dental composite material containing the calcined particles as a dental filler may also not match with that of natural teeth.

When the time employed for the calcination is less than one hour, it becomes impossible to obtain a desired mechanical strength of the calcined particles and also a desired refractive index thereof (which is in the range from 1.45 to 1.63), because the density of the covering material (i.e., the composite oxide as described above) does not become higher. As a result, sometimes a color tone of the tooth repaired with use of a dental composite material containing the calcined particles as a dental filler may not match with that of natural teeth.

As described above, with the present invention, it is possible to easily obtain the calcined particles of amorphous inorganic oxide by calcining the dried particles. The form of the calcined particles is almost the same as that of the dried particles, although shrinkage of the dried particles in the form is observed in some of the calcined particles.

If the particle diameter of the calcined particles thus obtained is larger than the desired value, the calcined particles are used as a dental filler after having adjusted the particle diameter to a desired value being in the range from 2 to 50000 nm, by crushing the calcined particles with a pulverizer or a grinder such as a mortar and a bowl mill. Especially, in the step (e) above, if the drying with a spray drier is not performed, or if the dried particles obtained from a generally known drying device are not crushed, it is desirable to crush the calcined particles to obtain the desired particle diameter.

Surface Treatment Step

The microparticles of amorphous inorganic oxide according to the present invention, namely the dried particles obtained in the step (e), the calcined particles obtained in the calcining step, and the crushed particles thereof, have the physical properties as described above, and can be used as the dental filler according to the present invention as they are, although the circumstances may be different in their applications.

When a refractive index of the microparticles of amorphous inorganic oxide should be adjusted to that of a hardenable resin which is used for production of a dental composite material, or when dispersibility of the microparticles in and adhesiveness thereof to the hardenable resin should be improved, it is desirable to subject the microparticles of amorphous inorganic oxide to a surface treatment (for improving the surfaces of the particles) with one or more organic metal compounds selected from the group consisting of organic silicon compounds, organic titanium compounds and organic zirconium compounds There is no specific restriction over a surface treatment method employed in the present invention, but the following method may be employed. Of these methods, the surface treatment methods (2) and (3), especially the surface treatment (3) as described below are preferably used. However, any known method of the surface treatment may be employed in the present invention.

(1) A method in which the mixture aqueous solution (4) containing a solid material comprising the microparticles of amorphous inorganic oxide having a form with a chain or network structure obtained in the step (d) is concentrated according to the necessity, then one or more organic metal compounds selected from the group consisting of organic silicon compounds, organic titanium compounds and organic zirconium compounds are added into the aqueous solution to cause the hydrolysis reaction of the organic metal compound for treating the surface of the solid material, and then the obtained solid material is dried. However, when the microparticles of amorphous inorganic oxide obtained by this method are required to subject the drying step and the calcining step as described above, the dispersibility of the microparticles (i.e., the dried particles or calcined particles) in a hardenable resin and the adhesiveness thereof to the resin are not improved, although the refractive index can be adjusted. Furthermore, when the microparticles of amorphous inorganic oxide obtained through the drying step or the calcining step are crushed for adjusting the average particle diameter thereof, some of the particles may be broken into small pieces and the surface-treated portion may be lost or dropped off during the crushing step, which spoils the original purpose of the surface treatment.

(2) A method in which the dried particles of amorphous inorganic oxide obtained in the step (e) are suspended in water and/or an organic solvent, then one or more organic metal compounds selected from the group consisting of organic silicon compounds, organic titanium compounds and organic zirconium compounds are added into the aqueous solution to cause the hydrolysis reaction of the organic metal compounds for treating the surfaces of the dried particles, and then the obtained microparticles are dried. However, when the microparticles obtained by this method are required to subject to the calcining step as described above, the dispersibility of the microparticles (i.e., the calcined particles) in a hardenable resin and the adhesiveness thereof to the resin are not improved, although the refractive index can be adjusted. Furthermore, when the microparticles of amorphous inorganic oxide obtained through the calcining step are crushed for adjusting the average particle diameter thereof, some of the particles may be broken into small pieces and the surface-treated portion may be lost or dropped off during the crushing step, which spoils the original purpose of the surface treatment.

(3) A method in which the calcined particles of amorphous inorganic oxide obtained in the calcining step are suspended in water and/or an organic solvent, then one or more organic metal compounds selected from the group consisting of organic silicon compounds, organic titanium compounds and organic zirconium compounds are added into the solution to cause the hydrolysis reaction of the organic metal compounds for treating the surfaces of the calcined particles, and then the obtained microparticles are dried. Because the microparticles of amorphous inorganic oxide obtained by this method are subjected to the surface treatment after having been calcined, the refractive index of the microparticles can be adjusted, and also the dispersibility of the microparticles in a hardenable resin and the adhesiveness thereof to the resin are easily improved.

Dental Composite Material

The dental composite material according to the present invention contains the dental filler and a hardenable resin.

The hardenable resin which may be used in the present invention includes, but not limited to, acrylic resin, methacrylic resin, epoxy resin, vinyl resin and urethane resin. From these hardenable resins, a resin is selected dependent upon an application of the dental composite material, but a mixture thereof can be used in this invention.

Any known method can be employed for producing the dental composite material, but generally the dental composite material can be produced by homogeneously mixing 10 to 50 parts by weight of the dental filler, 10 to 50 parts by weight of the hardenable resin, and 0.1 to 5 parts by weight of a catalyst for polymerization of the hardenable resin or a photo polymerization initiator thereof with agitation. In this case, it is possible to further add a stabilizer, a thickening agent, a coloring agent, a flavor preserving agent, an antibiotic agent, an aromatic substance and/or an auxiliary substance thereto.

The dental composite material produced as described above can advantageously be used in such applications as dental restoratives, dental adhesives, dental mill blanks, dental cements, artificial dentures, dental corrective devices, adhesive agents for dental correction, dental casting, dental coating or the like.

EXAMPLES AND COMPARATIVE EXAMPLES

The present invention is described below in detail with reference to examples and comparative examples. However, it should be noted that the present invention is not limited to the examples.

Preparation Example 1

Preparation of the Zirconium Oxide Hydrate

250 Kg of zirconium oxychloride ($ZrOCl_2.8H_2O$, produced by Taiyo Koko Co., Ltd) was added to 4375 Kg of pure water kept at the temperature of 15° C. with agitation to dissolve the zirconium oxychloride therein.

Furthermore, 250 L of ammonia water with the concentration of 15% by weight was slowly dripped with agitation in the aqueous solution of zirconium oxychloride for causing a neutralization reaction of the zirconium oxychloride at 15° C. to obtain a slurry containing a hydrate of zirconium oxide (sometimes hereinafter referred to as "the zirconium oxide hydrate"). The pH of the slurry thus obtained was 8.5.

Then the slurry was subjected to filtration, and the obtained cake-like substance was washed by pure water repeatedly to remove unreacted materials and byproducts in the neutralization reaction.

As a result, 860 Kg of the cake-like substance was obtained, and the substance contained a hydrate of zirconium oxide at the concentration of 10% by weight in terms of $ZrO_2$, and the remaining balance component was water.

Preparation of the Silicic Acid Solution

Preparation Example 2

10 Kg of water glass (produced by Asahi Glass S.I. Tec. Co., Ltd.) was diluted with 38 Kg of pure water, and then was treated with a cation-exchange resin (produced by Mitsubishi Chemicals. CO., Ltd.) to remove the alkali metal component contained therein. As a result, 9 Kg of an aqueous solution of silicic acid (sometimes hereinafter referred to as "the silicic acid solution") containing silicon compounds at the concentration of 4% by weight in terms of $SiO_2$ was prepared. The pH of the aqueous solution was about 3. Then, 10768 g of the silicic acid solution and 14860 g of pure water were mixed with each other, and 25628 g of the silicic acid solution in which the silicon compounds are contained at the concentration of 2% by weight in terms of $SiO_2$ was obtained.

Preparation of the Microparticles of Inorganic Oxide

Example 1

45800 g of pure water was added to 5416 g of the cake-like substance containing the zirconium oxide hydrate prepared in Preparation example 1, and 1024 g of a potassium hydrate reagent containing potassium hydroxide at the purity of 85% by weight (produced by Kanto Chemicals Co., Ltd.) was added with agitation to the above mixture solution to make the mixture solution alkaline, and then 10248 g of a hydrogen peroxide solution containing hydrogen peroxide at the concentration of 35% by weight (produced by Hayashi Pure Chemical Industries., Ltd.) was added to the resultant mixture solution.

Furthermore, the mixture aqueous solution thus obtained was agitated for one hour to peptize and dissolve the zirconium oxide hydrate in the aqueous solution. Then, 39991 g of ice water obtained by freezing pure water was added to the mixture aqueous solution. Thus, the temperature of the mixture aqueous solution elevated by an exothermic reaction of the peptization was cooled down to a level lower than 30° C. With the operation, 102400 g of the mixture aqueous solution containing zirconium components at the concentration of 0.5% by weight in terms of $ZrO_2$ (hereinafter referred to as "the example solution 1A") was obtained. The pH of the mixture aqueous solution was about 11.

47900 g of pure water was added to 3336 of a silica sol containing silica fine particles with the average particle diameter of 12 nm at the concentration of 30% by weight (produced by JGC Catalysts and Chemicals Ltd.: SI-30), and the mixture solution was fully agitated to obtain 51236 g of a silica sol containing the silica fine particles at the concentration of 2% by weight.

Then the silica sol was heated to 90° C., and then 12814 g of the silicic acid solution prepared in Preparation example 2 and 51200 g of the example solution 1A were gradually added with agitation to the silica sol over 10 hours. With the operation, 115250 g of the mixture aqueous solution with the pH of about 11 (hereinafter referred to as "the example solution 1B-(1)") was obtained.

Then, the example solution 1B-(1) was treated with a cation-exchange resin (produced by Mitsubishi Chemicals Co.: SK1BH) to remove the alkali metal component contained therein. With the operation, 117250 g of the mixture aqueous solution with the pH of about 9.5 (hereinafter referred to as "the example solution 1C-(1)") was obtained.

Furthermore, the example solution 1C-(1) was heated to 90° C., and then 12814 g of the silicic acid solution prepared in Preparation example 2 and 51200 g of the example solution 1A were gradually added with agitation to the example solution 1C-(1) over 10 hours. With the operation, 181264 g of the mixture aqueous solution with the pH of about 11 (hereinafter referred to as "the example solution 1B-(2)") was obtained.

Then, the example solution 1B-(2) was treated with a cation-exchange resin (produced by Mitsubishi Chemicals Co.: SK1BH) to remove the alkali metal component contained therein. With the operation, 182264 g of the mixture aqueous solution with the pH of about 9.5 (hereinafter referred to as "the example solution 1C-(2)") was obtained.

100200 g of the example solution 1C-(2) was put in an autoclave made from stainless steel (produced by Taiatsu Techno Co.), and was subjected to a hydrothermal treatment for 18 hours at 165° C. With the operation, 99750 g of the mixture aqueous solution containing a solid material comprising microparticles of inorganic oxide (hereinafter referred to as "the example solution 1D") was obtained.

Then, 500 g of the example solution 1D was taken out and was put in and spread on a petri dish with a thin layer (namely, in the state where the microparticles were not overlaid on each other), and was dried in a drier for 16 hours at 110° C. With the operation, 9.5 g of the dried particles comprising the microparticles of inorganic oxide (hereinafter referred to as "the example microparticles 1A-(1)") was obtained.

Then, 2050 g of the remaining example solution 1D was subjected to a ultra filtration unit to adjust the concentration of the solid material contained therein to 8% by weight, and was put in and spread on a petri dish with a relatively thick layer (namely, in the state where the microparticles were overlaid on each other) and dried in a drier for 16 hours at 110° C. With the operation, 4.5 g of the dried particles comprising microparticles of inorganic oxide (hereinafter referred to as "the example microparticles 1A-(2)") was obtained.

Each of the samples was taken out from the example microparticles 1A-(1) and the example microparticles 1A-(2) respectively, and was photographed with a field-emission electron microscope (produced by Hitachi High-Technologies Co.: FE-SEM). The photographs taken are as shown in FIG. 1 and FIG. 2 respectively.

From these photographs, it was confirmed that the example microparticles 1A-(1) has a form with a chain or network structure formed by the silica-based fine particles covered with a composite oxide comprising zirconium, silicon and oxygen, and a zonal substance or substances of the composite oxide having the same composition as described above, extended or bridged between or among the silica-based fine particles covered with the above composite oxide, and the example microparticles 1A-(2) has a form with a massive structure formed by entwining or coagulating the above materials of the inorganic oxide having a form with a chain or network structure.

Then, the example microparticles 1A-(2) were put in a mortar, and the aggregated particles or particles with a large diameter contained therein were crushed, and then 3.5 g of the crushed particles comprising microparticles of inorganic oxide having a form with a grain-like structure and having the particle diameters being not widely ranged (hereinafter referred to as "the example microparticles 1B") was obtained.

Then, 3.0 g of the example microparticles 1B was put in a quartz-made crucible, and the crucible was placed in an electric furnace (produced by Toyo Manufacturing Co., Ltd.), and then the microparticles were calcined for 3 hours at 800° C. With the operation, 2.1 g of the calcined particles comprising microparticles of inorganic oxide (hereinafter referred to as "the example microparticles 1C") was obtained.

Each of the samples taken out from the example microparticles 1B and the example microparticles 1C respectively was subjected to an X-ray diffractometer (RINT-1400, X-ray diffraction method) for measuring the X-ray diffraction peak, and any diffraction peak indicating crystallinity was not observed in any sample of the microparticles. As a result, it was found that all of the samples were in the amorphous state.

Furthermore, each of the samples taken out from the example microparticles 1B and the example microparticles 1C respectively was subjected to a field-emission transmittance electron microscope (produced by Hitachi High Technologies Inc.: FE-TEM) for qualitative analyses of the inorganic material covering the surfaces of the silica-based fine particles (sometimes hereinafter referred to as "the covering material"). Because the covering material has the same composition as that of the zonal substance or substances extended or bridged between or among the silica-based fine particles, the above sample used for this measurement was selected from the pieces of the zonal substance crushed in the crushing step as described above. As a result, it was found that the covering material was substantially composed of a composite oxide comprising zirconium, silicon and oxygen.

Furthermore, the particle diameters, refractive indexes and compression strengths of the samples taken out from the example microparticles 1B and the example microparticles 1C respectively were measured, and average values of such parameters were obtained. The results are shown in Table 1.

The above measurements were carried out by the methods as described below.

(a) Particle Diameter

A sample of the microparticles was added into a water-glycerin solution in which water and glycerin are contained at the weight ratio (i.e., water/glycerin) of 6/4, so that the content of the microparticles becomes 1% by weight. Then, a cell, in which the above mixture solution was put in, was set in a particle size analyzer based on the centrifugal sedimentation system (produced by Horiba Company: CAPA 700) to measure an average particle diameter of the microparticles. The measurement was performed under the conditions with a table's rotating speed of 1000 rpm and a particle size range of from 0.5 to 15 μm.

(b) Refractive Index 0.2 g of the microparticles as a sample and 0.2 g of the Cargilie standard refractive solution were homogeneously mixed to obtain a paste material. Then, a metallic ring with a thickness of 1 mm was placed on a slide glass plate, the paste material was set into the ring. Then, a cover glass sheet was placed thereon and slightly pressed toward the ring. The transparency of the paste material was visually checked.

(C) Compression Strength

A sample of the microparticles (having particle diameters in the range from 3 to 4 μm) was placed on a diamond platen of a micro-compression testing machine (produced by Simazu Corporation), and a load was given onto the sample to measure the loaded pressure and compressive deformation for obtaining a compression strength of the microparticles.

It should be noted that the measurement equipment and the measuring method employed in Example 1 are also employed in Examples 2 to 9 and Comparative Examples 1 to 10 as described below, unless otherwise specified.

Example 2 and Comparative Example 1

15000 g of the solution 2C-(2) was prepared by the same method as that employed for preparing the example solution 1C-(2) as described in Example 1.

Then, samples each having the weight of 4800 g were taken out from the solution 2C-(2), and each of the samples was put in an autoclave made from stainless steel (produced by Taiatsu Techno Co.) and subjected to a hydrothermal treatment for 18 hours at 90° C., at 110° C., and at 300° C. respectively. With the operation, mixture aqueous solutions each containing a solid material comprising microparticles of inorganic oxide (hereinafter referred to as "the comparative example solution 1D", "the example solution 2D-(1)", and "the example solution 2D-(2)" respectively) were obtained.

Each of the comparative example solution 1D, the example solution 2D-(1) and the example solution 2D-(2) was subjected to a ultra filtration unit to adjust the concentration of the solid material contained therein to 2% by weight, and then was dried for 16 hours at 110° C. in a drier, like in Example 1. With the operation, three samples of the dried particles comprising the microparticles of inorganic oxide (hereinafter referred to as "the comparative example microparticles 1A", "the example microparticles 2A-(1)" and "the example microparticles 2A-(2)" respectively) were obtained.

Then, each of the comparative example microparticles 1A, the example microparticles 2A-(1) and the example microparticles 2A-(2) was put in a mortar, and the aggregated particles or particles with a large diameter contained therein were crushed, like in Example 1. With the operation, three samples of the crushed particles comprising microparticles of inorganic oxide having a form with a grain-like structure and having the particle diameters being not widely ranged (hereinafter referred to as "the example microparticles 1B", "the example microparticles 2B-(1)" and "the example microparticles 2B-(2)" respectively) were obtained. The weights of the comparative example microparticles 1B, the example microparticles 2B-(1) and the example microparticles 2B-(2) thus obtained were 2.8 g, 2.1 g, and 2.3 g respectively.

Then, each of the comparative example microparticles 1B, the example microparticles 2B-(1), and the example microparticles 2B-(2) were calcined under the same conditions as those employed in Example 1. With the operation, three samples of the calcined particles comprising microcroparticles of inorganic oxide (hereinafter referred to as "the comparative example microparticles 1C", "the example microparticles 2C-(1)", and "the example microparticles 2C-(2)" respectively) were obtained.

Each of the samples taken out from the comparative example microparticles 1C, the example microparticles 2C-(1) and the example microparticles 2C-(2) respectively was subjected to an X-ray diffractometer (RINT-1400, X-ray diffraction method) for measuring the X-ray diffraction peak, to check it on whether the microparticles are amorphous ones or not, like in Example 1. Furthermore, each of the samples taken out from the comparative example microparticles 1C, the example microparticles 2C-(1) and the example microparticles 2C-(2) respectively was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 1C, the example microparticles 2C-(1) and the example microparticles 2C-(2) respectively were measured, and average values of such parameters were obtained, like in Example 1. The results are shown in Table 1.

Example 3 and Comparative Example 2

200 g of the microparticles 3B was prepared by the same method as that employed for preparing the example microparticles 1B as described in Example 1.

Then, samples each having the weight of 30 g were taken out from the microparticles 3B, and each of the samples was put in a quartz-made crucible which is placed in an electric furnace (produced by Toyo Manufacturing Co., Ltd.). In this state, the each of the samples was calcined for 3 hours at 350° C., 500° C., 800° C. and 1000° C. respectively. With the operation, four samples of the calcined particles comprising microparticles of inorganic oxide (hereinafter referred to as "the example microparticles 3C-(1)", "the example microparticles 3C-(2)", "the example microparticles 3C-(3)" and "the comparative example microparticles 2C") were obtained.

Each of the samples taken out from the example microparticles 3C-(1), the example microparticles 3C-(2), the example microparticles 3C-(3) and the comparative example microparticles 2C respectively was subjected to an X-ray diffractometer (RINT-1400, X-ray diffraction method) for measuring the X-ray diffraction peak, to check it on whether the microparticles are amorphous ones or not, like in Example 1. Furthermore, each of the samples taken out from the example microparticles 3C-(1), the example microparticles 3C-(2), the example microparticles 3C-(3) and the comparative example microparticles 2C respectively was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the example microparticles 3C-(1), the example microparticles 3C-(2), the example microparticles 3C-(3) and the comparative example microparticles 2C respectively were measured, and average values of such parameters were obtained, like in Example 1. The results are shown in Table 1.

Example 4

11500 g of the solution 4D was prepared by the same method as that employed for preparing the example solution 1D as described in Example 1.

Then, the example solution 4D was subjected to a ultra filtration unit to adjust the concentration of the solid material contained therein to 2% by weight, and then the resultant mixture solution was introduced into a spray drier (produced by NIRO ATOMIZER) for spray-drying the solid material contained therein, at the supply rate of 2 l/min and with the spray pressure of 0.45 Mpa. The temperature of a hot air stream employed in the spray-drying operation was 180° C. at the inlet for the spraying. With the operation, the dried particles comprising microparticles of inorganic oxide (hereinafter referred to as "the example microparticles 4A") was obtained. Then, 50 g of the example microparticles 4A was mixed with 100 g of ethanol, and the mixture solution was fully agitated and then left for one hour in the static state.

Then, four samples of the mixture solutions each containing microparticles, which were separated from a layer of about 0 to 3 cm from the supernatant, a layer of about 3 to 6 cm from the supernatant, a layer of about 6 to 9 cm from the supernatant, and a layer of about 9 to 12 cm (at the bottom) from the supernatant (hereinafter referred to as "the example solution 4E-(1)", "the example solution 4E-(2)", "the example solution 4E-(3)", and "the example solution 4E-(4)" respectively) were obtained.

Then, each of the example solution 4E-(1), the example solution 4E-(2), the example solution 4E-(3) and the example solution 4E-(4) was dried for 16 hours at 110° C. in a drier, like in Example 1. With the operation, four samples of the dried particles comprising the microparticles of inorganic oxide (hereinafter "the example microparticles 4A-(1)", "the example microparticles 4A-(2)", "the example microparticles 4A-(3)", and "the example microparticles 4A-(4)" respectively) were obtained. The weights of the example microparticles 4A-(1), example microparticles 4A-(2), example microparticles 4A-(3) and example microparticles 4A-(4) were 10 g, 10 g, 10 g, and 10 g respectively.

Then, each of the example microparticles 4A-(1), example microparticles 4A-(2), example microparticles 4A-(3) and example microparticles 4A-(4) was calcined under the same conditions as those employed in Example 1. With the operation, four samples of the calcined particles comprising microparticles of inorganic oxide (hereinafter referred to as "the example microparticles 4C-(1), "the example microparticles 4C-(2)", "the example microparticles 4C-(3)", and "the example microparticles 4C-(4)" respectively) were obtained.

Each of the samples taken out from the example microparticles 4C-(1), the example microparticles 4C-(2), the example microparticles 4C-(3) and the example microparticles 4C-(4) respectively was subjected to an X-ray diffractometer (RINT-1400, X-ray diffraction method) for measuring the X-ray diffraction peak, to check it on whether the microparticles are amorphous ones or not, like in Example 1. Furthermore, each of the samples taken out from the example microparticles 4C-(1), the example microparticles 4C-(2), the example microparticles 4C-(3) and the example microparticles 4C-(4) respectively was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the example microparticles 4C-(1), the example microparticles 4C-(2), the example microparticles 4C-(3), and the example microparticles 4C-(4) respectively were measured, and average values of such parameters were obtained, like in Example 1. The results are shown in Table 1.

Example 5 and Comparative Example 3

98 kg of the solution 5A was prepared by the same method as that employed for preparing the example solution 1A as described in Example 1.

Then, the silicic acid solution prepared in Example 2 and the solution 5A were added in two stages into 13480 g of a silica sol heated to 90° C., and the alkali metal component contained therein was removed in two stages by the same method as that employed in Example 1. The quantities of the silicic acid solution and the solution 5A to be added, and also the molar ratios ($SiO_2/ZrO_2$) in the mixture solutions when the silicon components contained in the silicic acid solution are expressed as $SiO_2$ (i.e., in terms of $SiO_2$) and the zirconium components contained in the solution 5A are expressed as $ZrO_2$ (i.e., in terms of $SiO_2$), are as shown in the table below.

|  | Silicic acid solution (g) | Solution 5A (g) | Molar ratio ($SiO_2/ZrO_2$) |
| --- | --- | --- | --- |
| Mixture solution 1 | 10784.0 | 43136.0 | 2/1 |
| Mixture solution 2 | 5055.0 | 20200.0 | 2/1 |
| Mixture solution 3 | 8087.5 | 32350.0 | 2/1 |
| Mixture solution 4 | 337.0 | 1348.0 | 2/1 |

200 g of the sample taken out from each of the mixture solutions 1 to 4 as described above (hereinafter referred to as "the comparative example solution 3C-(1)", "the example solution 5C-(1)", "the example solution 5C-(2)" and "the comparative example solution 3C-(2)" respectively) was put in a autoclave made from stainless steel (produced by Taiatsu Techno Co.), and then was subjected to a hydrothermal treatment for 16 hours at 160° C. With the operation, mixture aqueous solutions each containing a solid material comprising microparticles of inorganic oxide (hereinafter referred to as "the comparative example solution 3D-(1)", "the example solution 5D-(1)", "the example solution 5D-(2)" and "the comparative example solution 3D-(2)" respectively) were obtained.

Each of the comparative example solution 3D-(1), the example solution 5D-(1), the example solution 5D-(2) and the comparative example solution 3D-(2) was subjected to a ultra filtration unit to adjust the concentration of the solid material contained therein to 2% by weight, and then was dried for 16 hours at 110° C. in a drier like in Example 1. With the operation, four samples of the dried particles comprising the microparticles of inorganic oxide (hereinafter referred to as "the comparative example microparticles 3A-(1)", "the example microparticles 5A-(1)", "the example microparticles 5A-(2)" and "the comparative example microparticles 3A-(2)" respectively) were obtained.

Then, each of the comparative example microparticles 3A-(1), the example microparticles 5A-(1), the example microparticles 5A-(2) and the comparative example microparticles 3A-(2) was put in a mortar, and the aggregated particles or particles with a large diameter contained therein were crushed, like in Example 1. With the operation, four samples of the crushed particles comprising microparticles of inorganic oxide having a form with a grain-like structure and having the particle diameters being not widely ranged (hereinafter referred to as "the comparative example microparticles 3B-(1)", "the example microparticles 5B-(1)", "the example microparticles 5B-(2)" and "the comparative example microparticles 3B-(2)" respectively) were obtained. The weights of the comparative example microparticles 3B-(1), the example microparticles 5B-(1), the example microparticles 5B-(2) and the comparative example microparticles 3B-(2) thus obtained were 12 g, 11 g, 13 g, and 10 g respectively.

Then, each of the comparative example microparticles 3B-(1), the example microparticles 5B-(1), the example microparticles 5B-(2) and the comparative example microparticles 3B-(2) was calcined under the same conditions as those employed in Example 1. With the operation, four samples of the calcined particles comprising microparticles of inorganic oxide (hereinafter referred to as "the comparative example microparticles 3C-(1)", "the example microparticles 5C-(1)", "the example microparticles 5C-(2)" and "the comparative example microparticles 3C-(2)" respectively) were obtained.

Each of the samples taken out from the comparative example microparticles 3C-(1), the example microparticles 5C-(1), the example microparticles 5C-(2) and the comparative example microparticles 3C-(2) respectively was subjected to an X-ray diffractometer (RINT-1400, X-ray diffraction method) for measuring the X-ray diffraction peak, to check it on whether the microparticles are amorphous ones or not, like in Example 1. Furthermore, each of the samples taken out from the comparative example microparticles 3C-(1), the example microparticles 5C-(1), the example microparticles 5C-(2) and the comparative example microparticles 3C-(2) respectively was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 3C-(1), the example microparticles 5C-(1), the example microparticles 5C-(2) and the comparative example microparticles 3C-(2) respectively were measured, and average values of such parameters were obtained, like in Example 1. The results are shown in Table 1.

Example 6 and Comparative Example 4

60.0 kg of the solution 6A was prepared by the same method as that employed for preparing the example solution 1A as described in Example 1.

Then, 6740 g of the silicic acid solution prepared in Preparation example 2 and 26960 g of the solution 6A were added at two stages into 13480 g of silica sols heated to 50° C. and 80° C. respectively, and the alkali metal component contained therein was removed at two stages by the same method as that employed in Example 1.

Then, each of the samples taken out from the mixture solutions (hereinafter referred to as "the comparative example solution 4C" and "the example solution 6C") was put in an autoclave made from stainless steel (produced by Taiatsu Techno Co.), and then was subjected to a hydrothermal treatment for 16 hours at 160° C. With the operation, mixture aqueous solutions each containing a solid material comprising microparticles of inorganic oxide (hereinafter referred to as "the comparative example solution 4D" and "the example solution 6D" respectively) were obtained.

Then, Each of the comparative example solution 4D and the example solution 6D was subjected to a ultra filtration unit to adjust the concentration of the solid material contained therein to 2% by weight, and then was dried for 16 hours at 110° C. in a drier, like in Example 1. With the operation, two samples of the dried particles comprising the microparticles of inorganic oxide (hereinafter referred to as "the comparative example microparticles 4A" and "the example microparticles 6A" respectively) were obtained.

Then, each of the comparative example microparticles 4A and the example microparticles 6A was put in a mortar, and the aggregated particles or particles with a large diameter contained therein were crushed, like in Example 1. With the operation, two samples of the crushed particles comprising microparticles of inorganic oxide having a form with a grain-like structure and having the particle diameters being not widely ranged (hereinafter referred to as "the comparative example microparticles 4B" and "the example microparticles 6B)" respectively) were obtained. The weights of the comparative example microparticles 4B and the example microparticles 6B thus obtained were 12 g and 15 g respectively.

Then, each of the comparative example microparticles 4B and the example microparticles 6B was calcined under the same conditions as those employed in Example 1. With the operation, two samples of the calcined particles comprising microparticles of inorganic oxide (hereinafter referred to as "the comparative example microparticles 4C" and "the example microparticles 6C" respectively) were obtained.

Each of the samples taken out from the comparative example microparticles 4C and the example microparticles 6C respectively was subjected to an X-ray diffractometer (RINT-1400, X-ray diffraction method) for measuring the X-ray diffraction peak, to check it on whether the microparticles are amorphous ones or not, like in Example 1. Furthermore, each of the samples taken out from the comparative example microparticles 4C and the example microparticles 6C respectively was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 4C and the example microparticles 6C respectively were measured, and average values of such parameters were obtained, like in Example 1. The results are shown in Table 1.

Comparative Example 5

28 kg of the solution 7A was prepared by the same method as that employed for preparing the example solution 1A as described in Example 1.

Then, 6740 g of the silicic acid solution prepared in Example 2 and 26960 g of the example solution 7A were added all at once to 13480 g of a silica sol heated to 90° C., and the alkali metal component contained therein was removed at one stage by the same method as that employed in Example 1.

Then, a sample taken out from the mixture solution (hereinafter referred to as "the comparative example solution 5C") was put in an autoclave made from stainless steel (produced by Taiatsu Techno Co.), and then was subjected to a hydrothermal treatment for 16 hours at 160° C. With the operation, a mixture aqueous solution containing a solid material comprising microparticles of inorganic oxide (hereinafter referred to as "the comparative example solution 5D") was obtained.

Then, the comparative example solution 5D was subjected to a ultra filtration unit to adjust the concentration of the solid material contained therein to 2% by weight, and then was dried for 16 hours at 110° C. in a drier, like in Example 1. With the operation, a sample of the dried particles comprising the microparticles of inorganic oxide (hereinafter referred to as "the comparative example microparticles 5A") was obtained.

Then, the comparative example microparticles 5A was put in a mortar, and the aggregated particles or particles with a large diameter contained therein were crushed, like in Example 1. With the operation, a sample of the crushed particles comprising microparticles of inorganic oxide having a form with a grain-like structure and having the particle diameters being not widely ranged (hereinafter referred to as "the comparative example microparticles 5B") was obtained. The weight of the comparative example microparticles 5B thus obtained was 14 g.

Then, the comparative example microparticles 5B was calcined under the same conditions as those employed in Example 1. With the operation, a sample of the calcined particles comprising microparticles of inorganic oxide (hereinafter referred to as "the comparative example microparticles 5C") was obtained.

A sample taken out from the comparative example microparticles 5C was subjected to an X-ray diffractometer (RINT-1400, X-ray diffraction method) for measuring the X-ray diffraction peak, to check it on whether the microparticles are amorphous ones or not, like in Example 1. Furthermore, the sample taken out from the comparative example microparticles 5C was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 5C were measured, and average values of such parameters were obtained, like in Example 1. The results are shown in Table 1.

Example 7

135 g of the microparticles 7B was prepared by the same method as that employed for preparing example microparticles 1B as described in Example 1.

Then, 100 g of the sample taken out from the microparticles 7B was put in a glass vessel, and 18 g of ethanol (containing ethyl alcohol by 99.5% by weight and water by 0.5% by weight) and 12 g of γ-methacryloxypropyl trimethoxysilane were further added into the vessel. The resultant mixture was mixed with agitation for one hour, and then was dried in a drier for 16 hours at 110° C. With the operation, the surfaces of the sample microparticles were treated with hydrolyzate of γ-methacryloxypropyl trimethoxysilane, and 112 g of the surface-treated microparticles (hereinafter referred to as "the example microparticles 7BX") was obtained.

A sample taken out from the example microparticles 7BX was subjected to an X-ray diffractometer (RINT-1400, X-ray diffraction method) for measuring the X-ray diffraction peak, to check it on whether the microparticles are amorphous ones or not, like in Example 1. Furthermore, the sample taken out from the example microparticles 7BX was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the example microparticles 7BX were measured, and average values of such parameters were obtained, like in Example 1. The results are shown in Table 1.

Example 8

152 g of the microparticles 8C was prepared by the same method as that employed for preparing the example microparticles 1C as described in Example 1.

Then, 100 g of the sample taken out from the microparticles 8C was put in a glass vessel, and 18 g of ethanol (containing ethyl alcohol by 99.5% by weight and water by 0.5% by weight) and 12 g of γ-methacryloxypropyl triethoxysilane were further added into the vessel. The resultant mixture was mixed with agitation for one hour, and then was dried in a drier for 16 hours at 110° C. With the operation, the surfaces of the sample microparticles were treated with hydrolyzate of γ-methacryloxypropyl triethoxysilane, and 112 g of the surface-treated microparticles (hereinafter referred to as "the example microparticles 8CX") was obtained.

A sample taken out from the example microparticles 8CX was subjected to an X-ray diffractometer (RINT-1400, X-ray diffraction method) for measuring the X-ray diffraction peak, to check it on whether the microparticles are amorphous ones or not, like in Example 1. Furthermore, the sample taken out from the example microparticles 8CX was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the example microparticles 8CX were measured, and average values of such parameters were obtained, like in Example 1. The results are shown in Table 1.

Comparative Example 6

122 g of the microparticles 6B was prepared by the same method as that employed for preparing the comparative example microparticles 1B as described in Comparative Example 1.

Then, 100 g of the sample taken out from the microparticles 6B was put in a glass vessel, and 18 g of ethanol (containing ethyl alcohol by 99.5% by weight and water by 0.5% by weight) and 12 g of γ-methacryloxypropyl trimethoxysilane were further added into the vessel. The resultant mixture was mixed with agitation for one hour, and then was dried in a drier for 16 hours at 110° C. With the operation, the surfaces of the sample microparticles were treated with hydrolyzate of γ-methacryloxypropyl trimethoxysilane, and 112 g of the surface-treated microparticles (hereinafter referred to as "the comparative example microparticles 6BX") was obtained.

A sample taken out from the comparative example microparticles 6BX was subjected to an X-ray diffractometer (RINT-1400, X-ray diffraction method) for measuring the X-ray diffraction peak, to check it on whether the microparticles are amorphous ones or not, like in Example 1. Furthermore, the sample taken out from the comparative example microparticles 6BX was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 6BX were measured, and average values of such parameters were obtained, like in Example 1. The results are shown in Table 1.

Comparative Example 7

100 g of the microparticles of silica with the average particle diameter of 6 μm (produced by produced by JGC Catalysts and Chemicals Ltd.: Silica Microbeads P-1500 calcined at 450° C.) was put in a glass vessel. Then, 18 g of ethanol (containing ethyl alcohol by 99.5% by weight and water by 0.5% by weight) and 12 g of γ-methacryloxypropyl trimethoxysilane were added into the vessel. The resultant mixture was mixed with agitation for one hour, and then was dried in a drier for 16 hours at 110° C. With the operation, the surfaces of the microparticles were treated with hydrolyzate of γ-methacryloxypropyl trimethoxysilane, and 112 g of the surface-treated microparticles (hereinafter referred to as "the comparative example microparticles 7AX") was obtained.

A sample taken out from the comparative example microparticles 7AX was subjected to an X-ray diffractometer (RINT-1400, X-ray diffraction method) for measuring the X-ray diffraction peak, to check it on whether the microparticles are amorphous ones or not, like in Example 1. Furthermore, the sample taken out from the comparative example microparticles 7AX was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 7AX were measured, and average values of such parameters were obtained, like in Example 1. The results are shown in Table 1.

Comparative Example 8

A silica sol containing fine particles of silica having the average particle diameter of 17 nm with the concentration of 10% by weight in terms of $SiO_2$ (produced by JGC Catalysts and Chemicals Ltd.: Cataloid S-20L) was diluted with water, and 1867 g of the diluted silica sol containing fine particles of silica with the concentration of 3% by weight was obtained. Then, 12 g of an aqueous solution of NaOH with the concentration of 3% by weight and 407 g of an aqueous solution of zirconyl ammonium carbonate containing zirconium component with the concentration of 4% by weight in terms of $ZrO_2$ (produced by Daiichi Kigenso Kagaku Kogyou Co., Ltd.: Zircosol AC-7) were added to the diluted silica sol, and the mixture solution thus obtained was agitated for 15 minutes, and 2286 g of the mixture solution was obtained.

Then, the mixture solution was introduced into a spray drier (produced by NIRO ATOMIZER) for spray-drying the solid material contained therein, at the supply rate of 2 l/min and with the spray pressure of 0.5 Mpa. The temperature of a hot air stream employed in the spray-drying operation was 180° C. at the inlet for the spraying. With the operation, the dried particles comprising microparticles of inorganic oxide (hereinafter referred to as "the comparative example microparticles 8A") were obtained.

Then, the comparative example microparticles 8A were calcined for 3 hours at 650° C., and the calcined particles comprising microparticles of inorganic oxide (hereinafter referred to as "the comparative example microparticles 8C") were obtained.

A sample taken out from the comparative example microparticles 8C was subjected to an X-ray diffractometer (RINT-1400, X-ray diffraction method) for measuring the X-ray diffraction peak, to check it on whether the microparticles are amorphous ones or not, like in Example 1. Furthermore, the sample taken out from the comparative example microparticles 8C was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 8C were measured, and average values of such parameters were obtained, like in Example 1. The results are shown in Table 1.

Comparative Example 9

188 g of the microparticles 9C was prepared by the same method as that employed for preparing the comparative example microparticles 8C as described in Comparative Example 8.

Then, 100 g of the sample taken out from the microparticles 9C was put in a glass vessel, and 18 g of ethanol (containing ethyl alcohol by 99.5% by weight and water by 0.5% by weight) and 12 g of γ-methacryloxypropyl trimethoxysilane were further added into the vessel. The resultant mixture was mixed with agitation for one hour, and then was dried in a drier for 16 hours at 110° C. With the operation, the surfaces of the sample microparticles were treated with hydrolyzate of γ-methacryloxypropyl trimethoxysilane, and 112 g of the surface-treated microparticles (hereinafter referred to as "the comparative example microparticles 9CX") was obtained.

A sample taken out from the comparative example microparticles 9CX was subjected to an X-ray diffractometer (RINT-1400, X-ray diffraction method) for measuring the X-ray diffraction peak, to check it on whether the microparticles are amorphous ones or not, like in Example 1. Furthermore, the sample taken out from the comparative example microparticles 9CX was subjected to a field-emission transmittance electron microscope (produced by Hitachi High Technologies Inc.: FE-TEM) for qualitative analyses of the covering material as described above, to check it on whether the covering material is a composite oxide comprising zirconium, silicon and oxygen or not, like in Example 1.

Furthermore, the particle diameters, refractive indexes and compression strengths of the samples taken out from the comparative example microparticles 9CX were measured, and average values of such parameters were obtained, like in Example 1. The results are shown in Table 1.

paste 9CY-(2)", "the comparative example paste 10CY-(1)", "the comparative example paste 10CY-(2)" and "the comparative example paste 10CY-(3)" respectively) were obtained. Then, each of the paste materials was homogeneously filled in a mold coated by Teflon™, and a light beam was irradiated to the filled material for hardening it with polymerization of the polymerizable compounds. With the operation, five samples of the hardened composite materials (hereinafter referred to as "the example hardened-material

TABLE 1

| Example micro-particles No. | Comparative example micro-particles No. | Crystalinity | Presence of composite oxide | Average particle diameter (μm) | Refractive index | Compression strength (kgf/cm$^2$) |
|---|---|---|---|---|---|---|
| 1B | | Amorphous | ○ | 3.1 | 1.53 | 38 |
| 1C | | Amorphous | ○ | 3.1 | 1.55 | 42 |
| 2C-(1) | | Amorphous | ○ | 3.2 | 1.55 | 42 |
| 2C-(2) | | Amorphous | ○ | 3.3 | 1.55 | 45 |
| 3C-(1) | | Amorphous | ○ | 3.0 | 1.53 | 39 |
| 3C-(2) | | Amorphous | ○ | 3.1 | 1.54 | 39 |
| 3C-(3) | | Amorphous | ○ | 3.0 | 1.55 | 41 |
| 4C-(1) | | Amorphous | ○ | 2.1 | 1.55 | 43 |
| 4C-(2) | | Amorphous | ○ | 3.3 | 1.55 | 42 |
| 4C-(3) | | Amorphous | ○ | 5.7 | 1.55 | 41 |
| 4C-(4) | | Amorphous | ○ | 8.0 | 1.55 | 42 |
| 5C-(1) | | Amorphous | ○ | 3.4 | 1.55 | 43 |
| 5C-(2) | | Amorphous | ○ | 3.5 | 1.57 | 45 |
| 6C | | Amorphous | ○ | 3.1 | 1.55 | 42 |
| 7BX | | Amorphous | ○ | 3.2 | 1.53 | 39 |
| 8CX | | Amorphous | ○ | 3.0 | 1.53 | 42 |
| | 1C | Amorphous | Δ | 3.1 | 1.55 | 41 |
| | 2C | Crystalline | X | 3.2 | 1.56 | 45 |
| | 3C-(1) | Amorphous | X | 3.1 | 1.58 | 40 |
| | 3C-(2) | Amorphous | X | 3.0 | 1.47 | 30 |
| | 4C | Amorphous | X | 2.9 | 1.55 | 42 |
| | 5C | Amorphous | X | 3.2 | 1.55 | 42 |
| | 6BX | Amorphous | Δ | 3.3 | 1.53 | 39 |
| | 7AX | Amorphous | X | 5.8 | 1.45 | 14 |
| | 8C | Amorphous | X | 3.0 | 1.51 | 35 |
| | 9CX | Amorphous | X | 3.0 | 1.50 | 35 |

In Table 1 as shown above, the symbol of "○" indicates that the covering material is substantially composed of a composite oxide comprising zirconium, silicon and oxygen; the symbol of "Δ" indicates that the covering material is partially composed of such a composite oxide, and the symbol of "X" indicates that the covering material is substantially not composed of such a composite oxide.

Preparation of Composite Material

Example 9 and Comparative Example 10

130 g of urethane dimethacrylate and 70 g of ethylene glycol dimethacrylate were mixed with each other. Then, 2 g of camphorquinone and 4 g of dimethyl aminoethyl methacrylate were added and mixed therewith, and 206 g of the polymerizable compounds as a hardenable resin was obtained.

Five samples each containing 30 g of the polymerizable compounds were prepared. Then, 70 g of the microparticles taken out from each of the example microparticles 7BX, the example microparticles 8CX, the comparative example microparticles 6BX, the comparative example microparticles 7AX and the comparative example microparticles 9CX was added to the sample of the polymerizable compounds as described above. The resultant mixture was mixed with agitation for one hour, and five samples each containing 100 g of the paste material as a dental composite material (hereinafter referred to as "the example paste 9CY-(1)", "the example 9CZ-(1)", "the example hardened-material 9CZ-(2)", "the comparative example hardened-material 10CZ-(1)", "the comparative example hardened-material 10CZ-(2)" and "the comparative example hardened-material 10CZ-(3)" were obtained.

Furthermore, the X-ray radiopacity, transparency, and bending strength were measured for each of the example hardened-material 9CZ-(1), the example hardened-material 9CZ-(2), the comparative example hardened-material 10CZ-(1), the comparative example hardened-material 10CZ-(2), and the comparative example hardened-material 10CZ-(3). The results are shown in Table 2.

The measurements were carried out by the methods as described below.

(a) X-ray Radiopaque Contrast

The hardened composite materials were photographed on X-ray dental film sheets with use of an X-ray photographing device. Furthermore, an aluminum plate having a prespecified thickness was photographed simultaneously, and when the X-ray radiopacity of a composite material was regarded as 100% when the value was the same as that of the aluminum plate.

(b) Transparency

Each of the hardened composite materials was placed on a transparency testing paper sheet divided to white and black portions so that a half of the plate was on the black portion, and the transparency of the plate was observed on both the white and black portions. The evaluation was made on the following criteria.

O: White turbidity or reflected light was not observed, and no coloring was observed in the white portion. (This result means that the transparency is high.)

Δ: The black portion was a little whitened, and a slight coloring was observed in the white portion. (This result means that the transparency is slightly low.)

X: The black portion was a little whitened and a reflected light was observed, and a light-brown color was observed in the write portion. (This result means that the transparency was low.)

(c) Bending Strength

Each of the hardened composite materials was preserved in distilled water at 37° C. for 24 hours, and the sample was taken out from the distilled water, and was subjected to a test for measuring a bending strength with an Instron Versatile Testing Machine under the conditions with the inter-fulcrum distance of 20 mm and the cross head speed of 1 mm/minute. For this measurement, five test pieces (having a shape of a rectangular parallelepiped with the width of about 2 mm, the height of about 2 mm, and the length of about 25 mm) were prepared for each sample, and the average value was regarded as a bending strength of the sample.

TABLE 2

| Example hardened-material No. | Comparative example hardened-material No. | X-ray Radiopacity (%) | Transparency | Bending strength (kgf/cm$^2$) |
|---|---|---|---|---|
| 9CZ-(1) | | 143 | ○ | 1800 |
| 9CZ-(2) | | 141 | ○ | 2100 |
| | 10CZ-(1) | 25 or below | X | 10 |
| | 10CZ-(2) | 25 or below | X | 714 |
| | 10CZ-(3) | 125 | Δ | 1154 |

Figure 1:
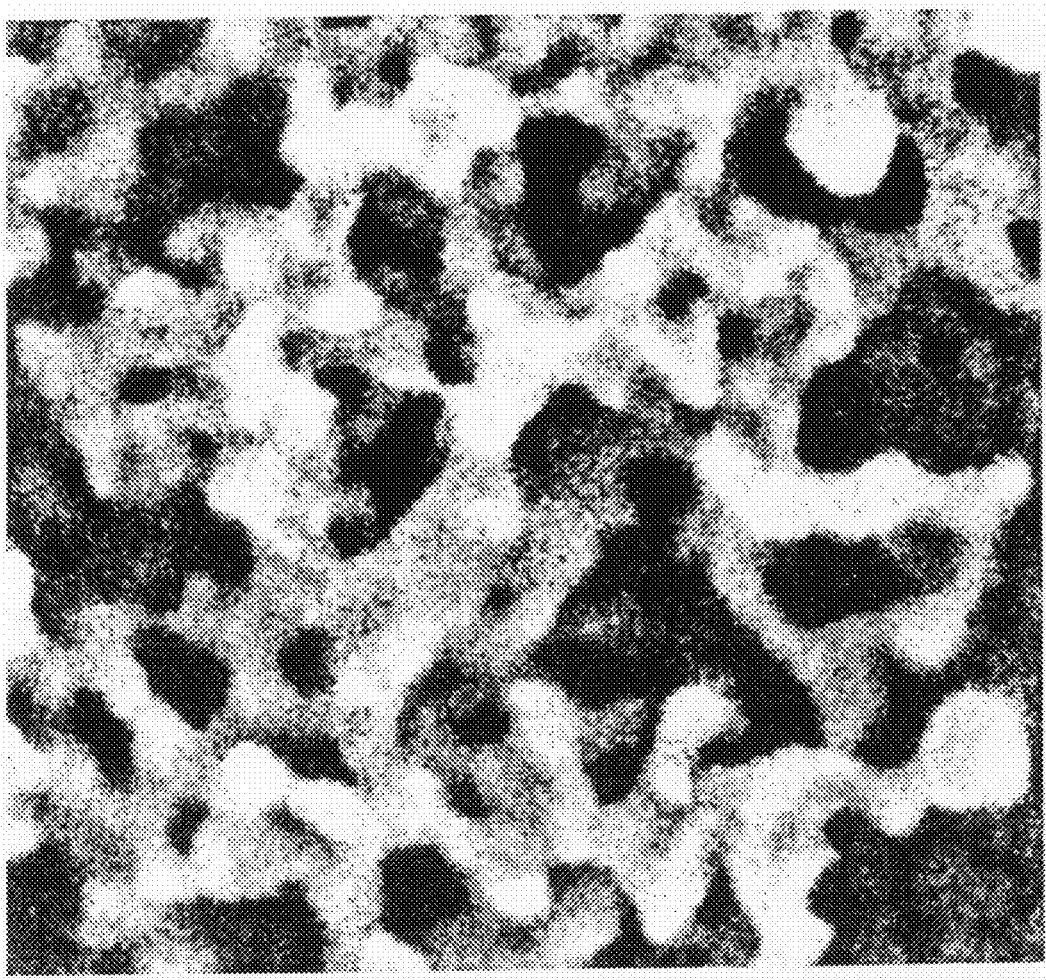
FIG. 1 shows a photograph taken for the sample of the example microparticles 1A-(1) produced in Example 1 by using a field-emission scanning electron microscope (with the magnifying power of 500,000)
Figure 2:
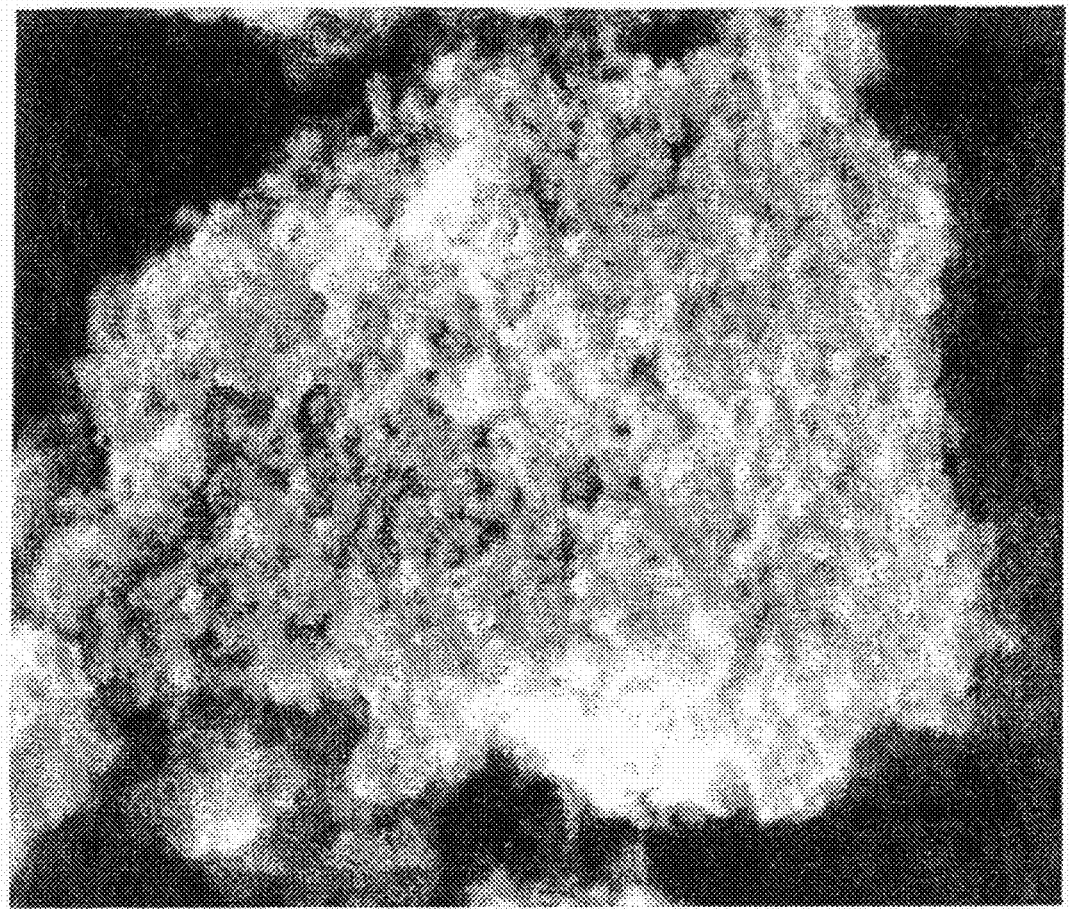
FIG. 2 shows a photograph taken for the sample of the example microparticles 1A-(2) produced in Example 1 by using a field-emission scanning electron microscope (with the magnifying power of 300,000).

The invention claimed is:

1. A dental filler comprising microparticles of amorphous inorganic oxide constituted by at least silica-based fine particles covered with a composite oxide comprising zirconium, silicon, and oxygen.

2. The dental filler according to claim 1, wherein said silica-based fine particles have an average particle diameter in the range from 2 to 300 nm.

3. The dental filler according to claim 1, wherein the microparticles are selected from dried particles or calcined particles of the amorphous inorganic oxide constituted by at least the silica-based fine particles covered with a composite oxide comprising zirconium, silicon, and oxygen.

4. The dental filler according to claim 3, wherein said dried particles or said calcined particles have a form selected from the group consisting of (1) a chain or network structure of the silica-based fine particles covered with the composite oxide comprising zirconium, silicon, and oxygen, and a zonal substance or substances of the composite oxide comprising zirconium, silicon, and oxygen, extending or bridging between or among the silica-based fine particles covered with the composite oxide; (2) a massive structure formed by entwining or coagulating materials of the amorphous inorganic oxide having a chain or network structure; and (3) a grain-like structure formed by crushing materials of the amorphous inorganic oxide having a chain or network structure or a massive structure.

5. The dental filler according to claim 3, wherein said calcined particles are obtained by calcining the dried particles of the amorphous inorganic oxide or by crushing thus calcined particles.

6. The dental filler according to claim 1, wherein the microparticles are those having been subjected to a surface treatment with one or more organic metal compounds selected from the group consisting of an organic silicon compound, an organic titanium compound and an organic zirconium compound.

7. The dental filler according to claim 1, wherein the dental filler has a refractive index in the range from 1.43 to 1.65.

8. The dental filler according to claim 1, wherein the microparticles have a form selected from the group consisting of a chain or network structure, a massive structure, or a grain-like structure.

9. The dental filler according to claim 8, wherein the massive structure is a spherical structure.

* * * * *